(12) United States Patent
Richards et al.

(10) Patent No.: US 11,756,002 B2
(45) Date of Patent: *Sep. 12, 2023

(54) IDENTIFICATION OF RELATIONSHIPS BETWEEN HEALTHCARE PRACTITIONERS AND HEALTHCARE CLINICS BASED ON BILLED CLAIMS

(71) Applicant: Milliman Solutions LLC, Seattle, WA (US)

(72) Inventors: Robert Richards, Salt Lake City, UT (US); David Muhlestein, Salt Lake City, UT (US)

(73) Assignee: Milliman Solutions LLC, Seattle, WA (US)

( * ) Notice: Subject to any disclaimer, the term of this patent is extended or adjusted under 35 U.S.C. 154(b) by 483 days.

This patent is subject to a terminal disclaimer.

(21) Appl. No.: 16/816,602

(22) Filed: Mar. 12, 2020

(65) Prior Publication Data
US 2021/0158942 A1 May 27, 2021

Related U.S. Application Data

(60) Provisional application No. 62/939,349, filed on Nov. 22, 2019.

(51) Int. Cl.
*G06F 16/90* (2019.01)
*G06F 16/28* (2019.01)
(Continued)

(52) U.S. Cl.
CPC ......... *G06Q 10/105* (2013.01); *G06F 16/24* (2019.01); *G06F 16/284* (2019.01);
(Continued)

(58) Field of Classification Search
CPC ........ G16H 40/20; G06F 16/90; G06F 16/288
See application file for complete search history.

(56) References Cited

U.S. PATENT DOCUMENTS 8,214,232 B2 7/2012 Tyler et al.
8,566,117 B1 10/2013 Troutt et al.
(Continued)

FOREIGN PATENT DOCUMENTS

CN 109739850 A * 5/2019

OTHER PUBLICATIONS

Madison et al., "Hospital-physician affiliation and patient treatments, expenditures, and outcomes," Health Service Research, 39(2), 257(22), Apr. 2004, 14 pages (Year: 2004).
(Continued)

*Primary Examiner* — Hosain T Alam
*Assistant Examiner* — Anthony G Gemignani
(74) *Attorney, Agent, or Firm* — Terrence J. Edwards; TechLaw Ventures, PLLC

(57) ABSTRACT

Identifying and quantifying a professional relationship between a practitioner and a clinic. A method includes identifying a clinic associated with a practitioner by assessing claims processed by the practitioner, identifying the clinic that are processed by the practitioner, and calculating a total quantity of claims processed by the practitioner. The method includes quantifying a relationship between the practitioner and the clinic based on the quantity of clinic claims and the total quantity of claims.

20 Claims, 10 Drawing Sheets

(51) Int. Cl.

| | | |
|---|---|---|
| *G16H 40/20* | (2018.01) | |
| *G16H 10/60* | (2018.01) | |
| *G06Q 40/12* | (2023.01) | |
| *G06Q 10/105* | (2023.01) | |
| *G06F 16/24* | (2019.01) | |
| *G16H 70/20* | (2018.01) | |
| *G06Q 10/10* | (2023.01) | |
| *G06Q 30/018* | (2023.01) | |
| *G16H 50/70* | (2018.01) | |
| *G06Q 10/0639* | (2023.01) | |
| *G06Q 50/26* | (2012.01) | |
| *G16H 40/00* | (2018.01) | |
| *G06F 21/60* | (2013.01) | |
| *G06F 21/62* | (2013.01) | |
| *G06Q 30/04* | (2012.01) | |
| *G06Q 40/08* | (2012.01) | |

(52) U.S. Cl.
CPC ............ *G06F 16/288* (2019.01); *G06F 16/90* (2019.01); *G06F 21/602* (2013.01); *G06F 21/6245* (2013.01); *G06Q 10/06398* (2013.01); *G06Q 10/10* (2013.01); *G06Q 30/0185* (2013.01); *G06Q 30/04* (2013.01); *G06Q 40/12* (2013.12); *G06Q 50/265* (2013.01); *G16H 10/60* (2018.01); *G16H 40/00* (2018.01); *G16H 40/20* (2018.01); *G16H 50/70* (2018.01); *G16H 70/20* (2018.01); *G06Q 40/08* (2013.01)

(56) References Cited

U.S. PATENT DOCUMENTS

| | | |
|---|---|---|
| 10,535,430 B1 | 1/2020 | Fischer et al. |
| 10,628,834 B1 | 4/2020 | Agarwal et al. |
| 10,991,457 B1 | 4/2021 | Hallemeier et al. |
| 2003/0083903 A1 | 5/2003 | Myers |
| 2005/0091080 A1 | 4/2005 | Biats, Jr. |
| 2010/0114607 A1 | 5/2010 | Kress et al. |
| 2010/0228564 A1 | 9/2010 | Kharraz Tavakol et al. |
| 2011/0125531 A1 | 5/2011 | Seare et al. |
| 2013/0073313 A1 | 3/2013 | Christakis et al. |
| 2013/0110533 A1 | 5/2013 | Paul et al. |
| 2014/0278479 A1 | 9/2014 | Wang et al. |
| 2015/0046181 A1 | 2/2015 | Adjaoute |
| 2015/0278462 A1 | 10/2015 | Smoley et al. |
| 2016/0019357 A1 | 1/2016 | Marzula et al. |
| 2016/0092649 A1* | 3/2016 | Denarie ................ G16H 20/10 705/2 |
| 2016/0132646 A1 | 5/2016 | Jones et al. |
| 2016/0188819 A1 | 6/2016 | Subramanian et al. |
| 2017/0017760 A1 | 1/2017 | Freese et al. |
| 2017/0142481 A1* | 5/2017 | Caruana ............... H04N 21/233 |
| 2018/0240195 A1 | 8/2018 | Bogle et al. |
| 2019/0073714 A1* | 3/2019 | Fidanza ................ G06Q 20/102 |
| 2019/0172564 A1* | 6/2019 | Chandra ................ G06N 20/00 |
| 2019/0206575 A1* | 7/2019 | Batey ................... G06K 9/6223 |
| 2019/0385126 A1 | 12/2019 | Morrow et al. |
| 2020/0043579 A1 | 2/2020 | McEwing |
| 2020/0272740 A1 | 8/2020 | Obee et al. |
| 2020/0411181 A1 | 12/2020 | Agnello et al. |
| 2021/0133605 A1 | 5/2021 | Greene et al. |
| 2021/0141834 A1 | 5/2021 | Mac Manus et al. |
| 2021/0158295 A1 | 5/2021 | Muhlestein et al. |
| 2021/0158452 A1 | 5/2021 | Muhlestein et al. |
| 2021/0158911 A1 | 5/2021 | Richards et al. |
| 2021/0158912 A1 | 5/2021 | Richards et al. |
| 2021/0158913 A1 | 5/2021 | Richards et al. |
| 2021/0158943 A1 | 5/2021 | Richards et al. |
| 2021/0158944 A1 | 5/2021 | Richards et al. |
| 2021/0158945 A1 | 5/2021 | Richards et al. |

OTHER PUBLICATIONS

Barnett et al., "Mapping Physician Networks with Self-Reported and Administrative Data," HSR: Health Service Research, 46:5 (Oct. 2011), pp. 1592-1609 (Year: 2011).

Bynum et al., "Assigning Ambulatory Patients and Their Physicians to Hospitals: A Method for Obtaining Population-Based Provider Performance Measurements," HSR: Health Services Research, 42:1, Part 1 (Feb. 2007), pp. 45-60 (Year: 2007).

* cited by examiner

IDENTIFICATION OF RELATIONSHIPS BETWEEN HEALTHCARE PRACTITIONERS AND HEALTHCARE CLINICS BASED ON BILLED CLAIMS

CROSS-REFERENCE TO RELATED APPLICATION

This application claims the benefit of U.S. Provisional Patent Application No. 62/939,349, filed Nov. 22, 2019, titled "IDENTIFICATION OF EMPLOYMENT RELATIONSHIPS BETWEEN HEALTHCARE PRACTITIONERS AND HEALTHCARE FACILITIES," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

The disclosure relates generally to the analysis of healthcare systems and particularly to identifying relationships between healthcare entities.

BACKGROUND

The healthcare industry is extraordinarily complex. Specifically, in the United States, relationships between healthcare practitioners, clinics, facilities, groups, and systems are complex and interwoven such that it can be challenging to identify relationships between different entities. One practitioner may see patients that are part of different systems, health insurance networks, or groups. Further, the practitioner may be associated with more than one facility or clinic. The interwoven relationships between healthcare entities makes it challenging to determine if a certain practitioner is associated with or employed by a certain facility, clinic, group, or system. Additionally, other relationships between practitioners, facilities, clinics, groups, and systems throughout the healthcare industry are difficult to identify and quantify.

In some instances, it is necessary or beneficial to understand the relationships between healthcare entities. For example, a health insurance provider seeking to create an in-network selection of providers may need to know which practitioners are associated with which facilities, clinics, groups, or systems. Further for example, a manufacturer or seller of medical devices or pharmaceuticals may benefit from understanding the business relationships between practitioners, facilities, clinics, groups, and systems. In some instances, for example, the manufacturer or seller may sell a medical device or pharmaceutical to a single group, and this would in turn lead to distribution of that medical device or pharmaceutical to hundreds of practitioners associated with the group. These relationships between healthcare entities are nearly impossible to identify or quantify.

In light of the foregoing, disclosed herein are systems, methods, and devices for identifying relationships between healthcare entities.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where.

DETAILED DESCRIPTION

Figure 1:
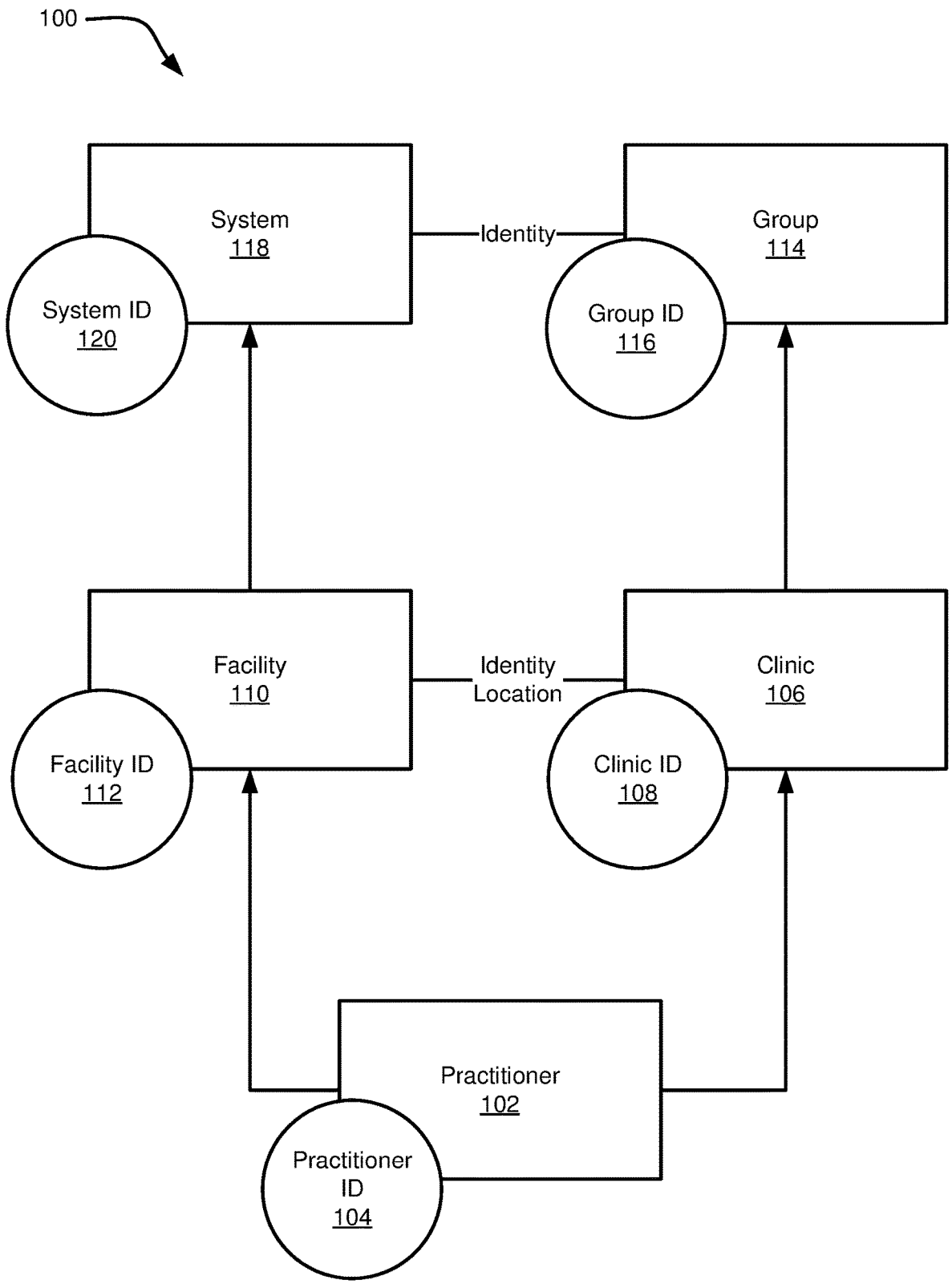
FIG. 1 is a schematic diagram of a framework outlining affiliations between healthcare entities.

Disclosed herein are systems, methods, and devices for identifying and quantifying relationships between healthcare entities. In an embodiment, relationships between healthcare practitioners and healthcare entities are identified and quantified based on billed claims.

Current understanding of the healthcare industry in the United States is extremely fragmented. In some instances, it is difficult or impossible to identify systems of care including financial, employment, and enrollment relationships between healthcare entities. The healthcare industry uses multiple data sources for storing billing, procedure, and facility records. There is no one data source that is ideal or reliable for identifying the numerous relationships between healthcare entities.

Embodiments of the disclosure begin at the level of individual practitioner billing and procedure codes and builds from there to identify and quantify relationships between other healthcare entities. By tracking the relationships of individual practitioners to higher level entities, the connections between practitioners and multiple other entities can be identified. This is an improved and more streamlined method when compared with viewing all organizations as discrete, mutually exclusive sets of practitioners.

Embodiments of the disclosure leverage multiple data sources to precisely and completely describe relationships between healthcare entities. Relationships between practitioners and other healthcare entities cannot be viewed as binary. There are multiple types of affiliations between healthcare entities, and each affiliation may be characterized in terms of its strength. An affiliation reported as merely binary (i.e. yes/no, exists/does not exist, and so forth) masks important information.

Embodiments of the disclosure interpret affiliation metrics based on an individualized perspective. For example, a physician's affiliation with a hospital has two perspectives: the physician's perspective and the hospital's perspective. The physician may view the hospital as a necessary portion of the practice that enables the physician to perform certain procedures. The hospital may view the physician as one of many, and the physician's procedures performed at the hospital may represent a very small portion of all procedures performed at the hospital. Understanding affiliations from both perspectives is more informative than viewing the affiliations from only one perspective.

Embodiments of the disclosure describe affiliations in terms of real-world activities that link practitioners to other healthcare entities. This can be performed by assessing disparate data sources in terms of real-world actions or relationships. Some actions, such as referrals or billing of office claims, may come naturally from a single data source. Other actions, such as geographic practice locations and clinic ownership, require synthesis of multiple data sources. The goal is not merely to represent the data sources, but to leverage the data sources to represent the real world. This results in new metrics and relationships that did not exist before. In embodiments of the disclosure, raw data is manipulated to identify real-world relationships that could not previously be identified or quantified.

Embodiments of the disclosure state affiliations between healthcare entities through action. For example, rather than querying practitioners and other healthcare entities about how they believe they are affiliated, it is more accurate to assess actual behaviors that illuminate real-world relationships free from spin, bias, ignorance, misunderstanding, or self-reported outcomes.

Before the structures, systems, and methods for identifying relationships between healthcare entities are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Referring now to the figures, FIG. 1 illustrates a framework 100 that outlines affiliations between healthcare entities. The framework 100 is built from the ground up and begins with the practitioner 102. The practitioner may be affiliated with facilities 110 and/or clinics 106. A facility 110 may be affiliated with a system 118. A clinic 106 may be affiliated with a group 114. There may be affiliations between systems 118 and groups 114 and between facilities 110 and clinics 106.

In an embodiment of the framework 100, a distinction is drawn between systems 118 that may own facilities 130, and groups 114 that may own clinics 106. This distinction is made for illustrative purposes and to increase the accuracy of conclusions drawn from assessing healthcare affiliations. In some instances, this distinction does not exist in the real world, and systems 118 and groups 114 functionally operate as the same entities. This serves as justification for the ground-up approach that permits individual practitioner behaviors to be leveraged to describe the relationships of higher-level entities with one another.

The practitioner 102 is a healthcare practitioner such as a physician (Doctor of Medicine), physician assistant, nurse practitioner, podiatrist, dentist, chiropractor, psychologist, optometrist, nurse midwife, clinical social worker, and so forth. The practitioner 102 may be a single person licensed to provide healthcare advice or guidance, perform procedures, prescribe medications, and so forth. The practitioner 102 may be a solo practitioner, may be associated with a group of other practitioners 102 in a clinic 106 or other group setting, may be employed by a facility 110 such as a hospital, may be employed as an in-house practitioner, and so forth. In some instances, it can be beneficial to identify and quantify the practitioner's 102 relationships with other entities such as clinic 106, facilities 130, groups 114, and systems 118.

The practitioner 102 may be associated with a practitioner ID 104. In some embodiments, the practitioner ID is an individual NPI (National Provider Identifier). In the United States, an individual National Provider Identifier (NPI) is a Health Insurance Portability and Accountability Act (HIPAA) administrative standard. An individual NPI is a unique identification number for covered healthcare providers. In the United States, covered healthcare providers, health plans, and healthcare clearinghouses are directed to use NPIs in administrative and financial transactions. It should be appreciated that the practitioner 104 may be associated with any unique identifier and does not need to be associated with a National Provider Identifier. The use of some other unique identifier does not depart from the scope of the disclosure. The practitioner ID 104 is a unique code associated with the practitioner 102. It should be appreciated that the practitioner ID 104 is any unique code associated with the practitioner 102 and can include other codes without departing from the scope of the disclosure.

The clinic 106 is a group of practitioners, a single practitioner, or some other entity that is primarily focused on the care of outpatients. The clinic 106 may be an outpatient clinic, an ambulatory care clinic, a physical therapy clinic, a specialist clinic, an urgent care clinic, an employer-funded in-house healthcare clinic, and so forth. The clinic 106 may be a group of practitioners that practice together at the same physical location or at different physical locations. The clinic 106 may include one or more practitioners 102 that practice telehealth care over the phone, over video communications, or by some other form of communication. The clinic 106 may be privately operated or publicly managed and funded. The clinic 106 may be suited for covering primary healthcare needs or specialized outpatient healthcare needs for populations of communities, in contrast with larger hospitals that offer specialized treatments and admit inpatients for overnight stays. The clinic 106 is not limited to only providing outpatient care.

The clinic 106 may be associated with an clinic ID 108. In some embodiments, the clinic ID 108 is an organization NPI (National Provider Identifier). In the United States, an organization National Provider Identifier (NPI) is a Health Insurance Portability and Accountability Act (HIPAA) administrative standard. An organization NPI is a unique identification number for covered healthcare clinics. The clinic ID 108 is a unique code associated with the clinic 106. If the clinic 106 has multiple geographic locations, then each of the multiple geographic locations for the clinic 106 may have a unique clinic ID 108. In some instances, two or more locations for the same clinic 106 share a clinic ID 108. It should be appreciated that the clinic 106 may be associated with any unique identifier and does not need to be associated with an organization NPI. The use of some other unique identifier does not depart from the scope of the disclosure.

The facility 110 is a physical or virtual healthcare location where an individual can receive care from a practitioner 102. The facility 110 may include hospitals, ambulatory surgical centers, birth centers, blood banks, dialysis centers, hospice centers, imaging and radiology centers, mental health and addiction treatment centers, nursing homes, orthopedic and other rehabilitation centers, telehealth systems, and so forth. In some implementations, it is not necessary to provide a formal definition for a facility 110 versus a clinic 106, and this distinction can be drawn based on the factual circumstances of various healthcare entities.

In an example embodiment, the facility 110 is linked to a facility ID 112. In some embodiments, the facility ID 112 is a Centers for Medicare and Medicaid Services (CMS) Certification Number, which is referred to as a CCN. In the United States, the CCN is the facility's 110 unique identification code that is linked to the facility's 110 provider agreement for Medicare billing. In some instances, the CCN is referred to as the facility's 110 "provider number." The facility ID 112 is used for submitting and reviewing the facility's 110 cost reports. It should be appreciated that the facility 110 may be associated with any unique identifier and does not need to be associated with a CCN. The use of some other unique identifier does not depart from the scope of this disclosure.

The group 114 is a healthcare entity that owns one or more clinics 106. The group 114 may alternatively be referred to as a "provider group." In some instances, there is no real-world distinction between groups 114 and systems 118, and this distinction is made in the systems, methods, and devices disclosed herein for the purpose of improving analytics on various healthcare entities. In some instances, a single healthcare entity may be referred to as a group 114 and as a system 118 for purposes of improving the analytics described herein.

The group 114 may be associated with a group ID 116. In some embodiments, the group ID 116 is a PAC ID (PECOS Associate Control ID) assigned by PECOS (Provider Enrollment, Chain and Ownership System). The PECOS is a system used in the United States and enables practitioners and other healthcare facilities to register with the Centers for Medicare and Medicare Services. PECOS is the Provider, Enrollment, Chain, and Ownership System. The system 118 may further be associated with the group ID 116. In some cases, a group 114 and a system 118 are the same entity and are associated with the same group ID 116. In some cases, a group 114 and a system 118 are separate entities to the degree that the group 114 is associated with its own group ID 116 and the system 118 is associated with its own system ID 120.

The system 118 is a healthcare entity that owns one or more facilities 110. In some instances, there is no real-world distinction between groups 114 and systems 118, and this distinction is made in the systems, methods, and devices disclosed herein for the purpose of improving analytics on various healthcare entities. In some instances, a single healthcare entity may be referred to as a group 114 and as a system 118 for purposes of improving the analytics described herein.

There are numerous metrics that can be calculated based on the relationships between practitioners 102, clinics 106, facilities 110, groups 114, and systems 118. In some cases, the metrics are determined based on claims billed by any of the entities described in FIG. 1. Some basic affiliation metrics that can be calculated include practitioner billing metrics, clinic billing metrics, practitioner enrollment metrics, clinic enrollment metrics, practitioner-group billing metrics, group billing metrics, practitioner-facility procedure volume metrics, facility procedure volume metrics, practitioner-facility employment metrics, facility-clinic distance metrics, and others. The practitioner billing metric is the proportion of a practitioner's total office claims billed to a certain clinic associated with a specific clinic ID 108. The clinic billing metric is the proportion of total office claims billed under a clinic performed by a given practitioner. The practitioner enrollment metric is the clinics at which a practitioner is enrolled in the PECOS. The clinic enrollment is the practitioner(s) enrolled in the PECOS under a clinic. The practitioner-group billing is the proportion of the practitioner's office claims billed under any of the group's clinics. The group billing is the proportion of all office claims billed under any of the group's clinics that were performed by a specific practitioner. The practitioner-facility procedure volume is the proportion of a practitioner's total procedure claims performed at each facility. The facility-procedure volume is the proportion of the procedures performed at the facility performed by each practitioner. The practitioner-facility employment is the level of confidence that the practitioner is employed by a given facility. The facility or clinic distance is the distance between a clinic and a facility in miles or some other distance measurement.

Figure 2:
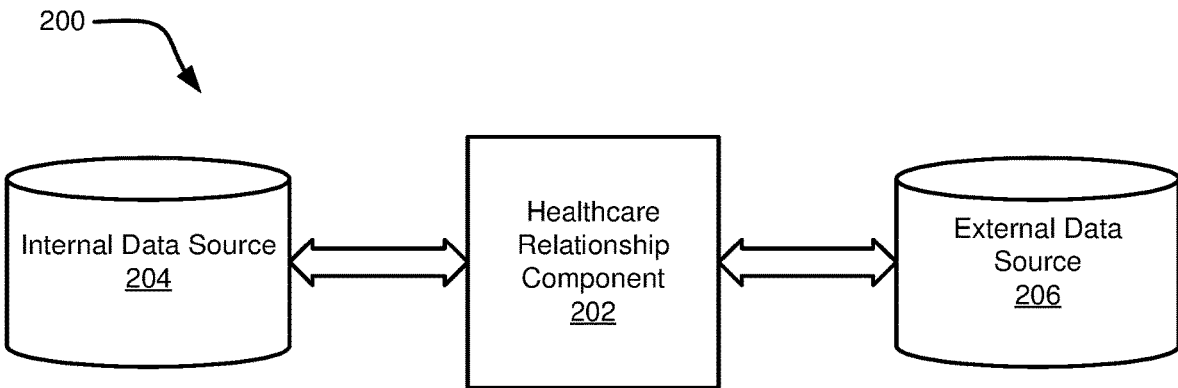
FIG. 2 is a schematic diagram of a system for data communication between a healthcare relationship component and internal and external data sources.

FIG. 2 is a schematic diagram of a system 200 for data communication between a healthcare relationship component 202 and internal and external data sources. The healthcare relationship component 202 identifies and quantifies professional relationships between healthcare entities. The healthcare relationship component 202 performs these calculations based on real-world claim data that can be stored in a combination of internal and external data sources. The healthcare relationship component 202 may communicate with one or more of an internal data source 204 and an external data source 206. The internal data source 204 may be a database, data store, or other memory device that is "internal" to the healthcare relationship component 202 or is managed by the same entity as the healthcare relationship component 202. The external data source 206 may be a database, data store, or other memory device that is "external" to the healthcare relationship component 202 or is managed by some other entity such that the healthcare relationship component 202 must access that data by way of an Application Program Interface (API), by receiving a file, by accessing an external server, and so forth.

In an embodiment, the healthcare relationship component 202 communicates directly with an external data source 206 that is managed or owned by a third-party entity. In an embodiment, the external data source 206 is owned and managed by the Medicare system operated by the United States government, or by some other entity that has been tasked with managing data for the Medicare system. In an embodiment, the external data source 206 is a relational database, and the healthcare relationship component 202 communicates with the relational database by way of an Application Program Interface (API). In an embodiment, the external data source 206 is an encrypted hard-drive that has been shared with the healthcare relationship component 202. In an embodiment, the external data source 206 is a virtual data center, and the healthcare relationship component 202 access the data on a virtual server after signing in or undergoing some other authentication step.

In an embodiment, the healthcare relationship component 202 communicates with an internal data source 204 that is not managed by some other third-party entity. The internal data source 204 may include a file that has been downloaded or otherwise received from some third-party entity, such as the Medicare system. After the file has been downloaded, the file can be managed and manipulated by the healthcare relationship component 202. The internal data source 204 may include an encrypted hard-drive or downloaded encrypted file that is provided by a third-party, such as the Medicare system.

The healthcare relationship component 202 may receive and translate information from multiple different sources. In an example implementation, the healthcare relationship component 202 receives enrollment information from a central data warehouse that may be operated internally or by a third-party. The healthcare relationship component 202 further receives claims data from a different source, for example via a secure connection to a virtual data store by way of an API, by accessing an encrypted hard drive, or accessing an encrypted file that has been downloaded by way of a network connection.

In an embodiment, the data stored in the internal data source 204 has been "cleaned" or pared down to only include necessary or critical information. This can be beneficial to ensure the totality of the data is a usable size that can be efficiently queried, analyzed, and manipulated. For example, the raw data retrieved from the external data source 206 may include numerous data fields that are not necessary for identifying a certain relationships between healthcare entities. The unnecessary data may be eliminated, and only the necessary data may be stored on the internal data source 204. In an embodiment, the raw data is cleaned and stored in a relational database.

In an embodiment, the healthcare relationship component 202 analyzes information stored in the internal data source 204 and/or the external data source 206 by identifying relationships between individual practitioners 102 and their associated clinics 106 and groups 114. In an example use-case, the healthcare relationship component 202 identifies that Doctor A is performing work for Clinic B. The healthcare relationship component 202 then identifies all of the practitioners that associate with Clinic B and assesses the carrier claims billed by those practitioners. The healthcare relationship component 202 aggregates the claim information for all practitioners in Clinic B and combines the information in an effort to answer specific questions, such as whether a certain practitioner is employed by a facility.

The healthcare relationship component 202, or some other module or component in communication with the healthcare relationship component 202, may create intermediary files or tables within a relational database. The intermediary files or tables may include certain information columns that are pertinent to answer a specific question, such as identifying or quantifying a relationship between two or more healthcare entities. This can be beneficial to ensure that each intermediary file or table is no bigger than it needs to be to include all necessary information for answering the specific question. This decreases the amount of disc storage and/or Random Access Memory (RAM) needed to analyze the information and calculate the answer to the specific question.

Figure 3:
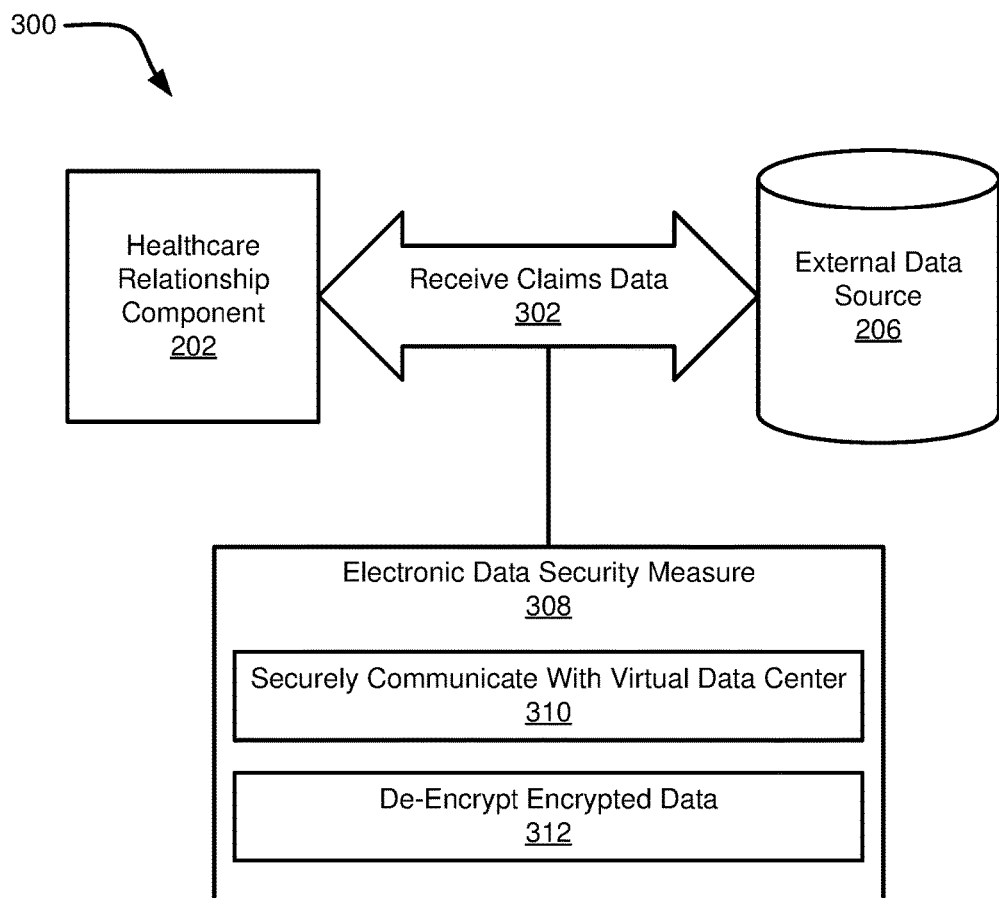
FIG. 3 is a schematic diagram of a system for performing electronic data security measures on data received from an external data source.

FIG. 3 is a schematic diagram of a system 300 for performing electronic data security measures on data received from the external data source 206. The healthcare relationship component 202 receives claims data (see 302) from an external data source 206. The claims data may include carrier claims, facility claims, and other claims processed by private or public healthcare entities. Claims data includes sensitive information such protected personal information (PPI) and personal identifiable information (PII), and therefore, the claims data must be encrypted or otherwise secured.

In an embodiment, the healthcare relationship component 202 receives claims data by securely communicating with a virtual data center (see 310). The virtual data center may be provided by a private or public healthcare entity. In an embodiment, an account is created for a user associated with the healthcare relationship component 202, and the user can sign into the virtual data center with the account. The user can then access the data stored in the virtual data center 310 by way of the account. The data may be encrypted or non-encrypted based on the security measures of the virtual data center. In an embodiment, the data is non-encrypted when viewed by way of a network connection, and the data is encrypted if downloaded for offline use and manipulation. If the data is downloaded in an encrypted form, then the data must be de-encrypted prior to analysis and manipulation.

In an embodiment, the healthcare relationship component 202 receives claims data by way of an encrypted hard-drive. The encrypted hard-drive may be provided by the source of the data, such as private or public healthcare entity. In an embodiment, the healthcare relationship component 202 receives claims data by way of an encrypted file that has been downloaded by way of a network connection. The healthcare relationship component 202 undergoes an electronic data security measure 308 by de-encrypting the claims data (see 312).

Figure 4:
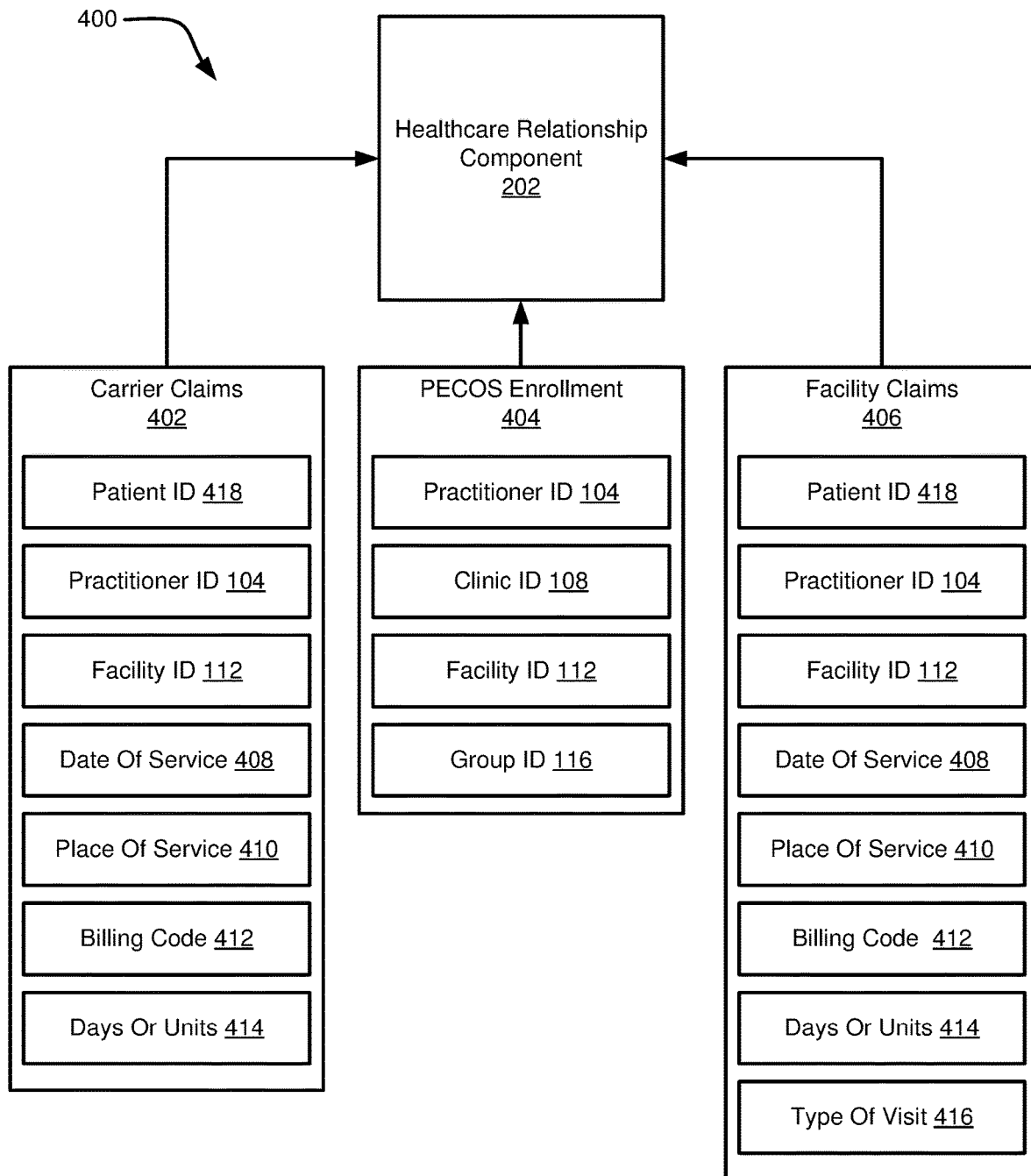
FIG. 4 is a schematic diagram of a data flow to a healthcare relationship component, including carrier claims data, PECOS enrollment data, and facility claims data.

FIG. 4 is a schematic diagram of a data flow 400 for identifying and quantifying a relationship between a practitioner and a clinic. The healthcare relationship component 202 receives carrier claims 402, PECOS enrollment 404 information, and facility claims 406. The carrier claims 402 are billed claims submitted by a practitioner 102 for one or more services, procedures, devices, pharmaceuticals, and so forth administered to a patient. The PECOS enrollment 404 information includes a listing of enrolled persons, clinics, facilities, groups, and so forth in the PECOS. The facility claims 406 are billed claims submitted by a facility 110 for one or more services, procedures, devices, pharmaceuticals, and so forth administered to a patient at the facility. Oftentimes, the facility is a hospital, surgical center, instant healthcare clinic, and so forth.

The PECOS is the Provider Enrollment, Chain, and Ownership System used in the United States. The PECOS was launched by the Medicare healthcare program in the United States and serves as a single national database for all physician and nonphysician healthcare professionals enrolled in Medicare. When a practitioner enrolls in the PECOS, the practitioner receives a practitioner ID 104 in the form of an individual NPI. When a clinic enrolls in the PECOS, the clinic receives a clinic ID 108 in the form of an organization NPI. Practitioners 102, clinics 106, and other entities can receive an identification without enrolling in the PECOS. Specifically, a practitioner 102 can receive an individual NPI and a clinic 106 can receive an organization NPI without rolling in the PECOS. Enrollment in the PECOS results in an assignment of a PAC ID, upon a practitioner 102 or other entity's first registration, and also of enrollment IDs for all enrollments (including the first enrollment). The individual NPI and the organization NPI are separate identifications assigned in the NPPES system, and these identifiers are also included in the PECOS enrollment data. Entities are often enrolled in the PECOS under the same PAC ID. Practitioner 102 enroll under their own PAC ID but may then reassign billing rights to another PECOS enrollment such as a group or other organization.

A carrier claim 402 is a non-institutional medical billing claim submitted by a practitioner 102 for professional services. The carrier claim 402 may be billed for outpatient or inpatient services. The carrier claims 402 used by the healthcare relationship component 202 may include carrier claims 402 submitted through the Medicare system implemented in the United States and may additionally include carrier claims for private entities such as private health insurance agencies. If the carrier claims 402 include Medicare claims, then the carrier claim may be submitted on the health insurance claim form CMS-1500 used by the United States Medicare system.

Carrier claims 402 include information about a service provided by a practitioner 102 in an outpatient or inpatient setting. In some instances, only a portion of the information included in the carrier claim 402 is relevant to the analysis of whether a relationship exists between a practitioner and a clinic. Carrier claims 402 may include a patient identification (ID) 418, which may include a numerical or alphanumerical code assigned to the patient, and may further include the patient's name, address, or other contact information. Carrier claims 402 further include a practitioner ID 104 which may specifically include an individual NPI. The carrier claim 402 may include a clinic ID 108 identifying which clinic the practitioner is billing the claim under, or which clinic the procedure is associated with. The carrier claim 402 includes an indication of the date of service 408 when the service was performed or on what date the service began, if the service extended over multiple days. The carrier claim 402 includes an indication of the place of service 410, and this may be a numerical or alphanumerical code identifying a facility, and may also include a name, address, or other contact information for the facility. The carrier claim 402 includes one or more billing codes 412 identifying the services or procedures that were performed by the practitioner 102. The billing code 412 may include a Healthcare Common Procedure Coding System (HCPCS) code. The carrier claim 402 may further include an indication of the days or units 414 indicating a duration of time the procedure occurred.

Carrier claims 402 may include additional information not illustrated in FIG. 4, For example, carrier claims 402 may include an indication of whether the bill is being submitted through a government-funded plan such as Medicare, Medicaid, Tricare, or CHAMPVA, or a private health insurance plan. The carrier claim 402 may include insurance information, such as the insured's ID number, name, address, birth date, policy name, group number, policy number, whether there is an additional health benefit plan, and so forth. The patient ID 418 information may include the patient's name, address, telephone number, and so forth. Additionally, the claim data may be cleaned before being received such that no personal information is included in the claim. In an embodiment, the carrier claim 402 includes anonymous patient identifiers and some demographic information such as country of residence, Medicare enrollment, Medicare eligibility status, sex, age, and broad race or ethnicity categories. Other more personal information might be cleaned from the carrier claim 402 prior to being assessed by the systems described herein.

The carrier claim 402 may include an indication of whether the patient's condition is related to employment, an automobile accident, or some other accident. The date of service 408 information may include an indication of what date the current illness, injury, pregnancy, or other condition began. The date of service 408 may further include other applicable dates. The carrier claim 402 may include information about what dates the patient was unable to work in his or her current occupation, dates of hospitalization related to the current services, charges made to an outside lab in relation to the current services, and so forth. The carrier claim 402 may include information about a referring provider or other source, such as the referring provider's individual NPI. The billing code 412 may include a diagnosis code or an indication of the nature of illness or injury and may further include a CPT or HCPCS code indicating the procedures, services, or supplies used in connection with the billed claim. For each billing code 412 listed in the carrier claim 402, there is also an indication of the date of service, the place of service, the diagnosis pointer, the charges, the days or units, and the rendering provider's practitioner ID 104 for that service, procedure, or supply. The carrier claim 402 may further include a federal tax ID number for the practitioner 102, a patient account number relating to the practitioner's practice, a total charge and the amount paid. The carrier claim 402 additionally includes information on the facility where the service, procedure, or supply was administered to the patient. The information on the facility may include the name, address, contact information, or a clinic ID 108 or facility ID 112 related to the facility.

The PECOS enrollment 404 may be a single file or electronic relational database that includes a listing of all practitioners, clinics, facilities, groups, and so forth that are enrolled in the PECOS. All entities enrolled in the PECOS are assigned an identification number. For practitioners 102 enrolled in the PECOS, a practitioner ID 104 is assigned in the form of an individual NPI. For clinics 106 enrolled in the PECOS, a clinic ID 108 is assigned in the form of an organization NPI. Practitioners 102, clinics 106, and other entities can receive an identification without enrolling in the PECOS. Specifically, a practitioner 102 can receive an individual NPI and a clinic 106 can receive an organization NPI without rolling in the PECOS. Enrollment in the PECOS results in an assignment of a PAC ID, upon a practitioner 102 or other entity's first registration, and also of enrollment IDs for all enrollments (including the first enrollment). The individual NPI and the organization NPI are separate identifications assigned in the NPPES system, and these identifiers are also included in the PECOS enrollment data. Entities are often enrolled in the PECOS under the same PAC ID. Practitioner 102 enroll under their own PAC ID but may then reassign billing rights to another PECOS enrollment such as a group or other organization.

The facility claims 406 may include similar information when compared with carrier claims 402. If the facility claims 406 include Medicare claims, then the facility claims may be submitted on the health insurance claim form UB-40 used by the United States Medicare system. The facility claims 406 may include, for example, the patient ID 418, practitioner ID 104, facility ID 112, date of service 408, place of service 410, billing code 412, days or units 414, and an indication of the type of visit 416. The indication of the type of visit 416 may be a numerical code indicating whether the visit was an emergency, an outpatient visit, an inpatient visit, and so forth.

Facility claims 406 may include additional information not illustrated in FIG. 4. The facility claims 406 may include all of the information listed above with reference to the carrier claims 402. The facility claims 406 may additionally include information on when the patient was admitted to the facility, the condition codes pertaining to why the patient was admitted to the facility, and the dates the patient was in-patient or out-patient at the facility. The facility claim 406 may include numerous practitioner IDs 104 pertaining to each of the numerous practitioners 102 who assisted in the patient's care while the patient was at the facility 110. Each service, procedure, or supply administered to the patient during the patient's stay at the facility 110 may linked to a certain practitioner 102.

Figure 5:
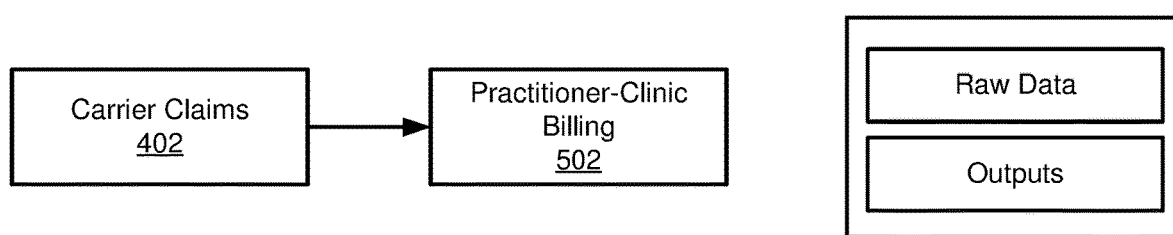
FIG. 5 is a data flow chart for identifying and quantifying a practitioner-clinic billing relationship.

FIG. 5 is a schematic diagram of a data framework for identifying a billing relationship between a practitioner 102 and a clinic 106. The analysis described in connection with FIG. 5 can be used to determine at what clinic(s) 106 a practitioner 102 is billing for services. The billing relationship between practitioners 102 and clinics 106 is based on office-based carrier claims 402. In the United States, when a practitioner 102 bills Medicare for office-based services, an clinic ID 108 is provided on the carrier claim 402. The practitioner-clinic billing 502 relationship is analyzed and quantified based on the data associated with carrier claims 402. The practitioner-clinic billing 502 relationship is measured by calculating the percentage of a practitioner's 102 total office-based claims that are billed under the clinic ID 108 associated with the clinic 106. If a practitioner 102 bills more frequently under a first clinic than a second clinic, the practitioner 102 is more strongly affiliated with the first clinic.

$$\text{Practitioner Billing}_{c'p'} = \frac{\text{Number of Claims}_{c'p'}}{\sum_{c \in C_{p'}} \text{Number of Claims}_{cp'}}$$

$$\text{Clinic Billing}_{c'p'} = \frac{\text{Number of Claims}_{c'p'}}{\sum_{p \in P_{c'}} \text{Number of Claims}_{c'p}}$$

In the equations above, c' is the clinic 106 being referenced by the final metric and p' is the practitioner 102 being referenced by the final metric. $C_{p'}$ is a set comprising a plurality of clinics c (including c') at which the practitioner p' bills claims, and $P_{c'}$ is a set comprising a plurality of practitioners p (including p') billing at the clinic c'. A Number of Claims$_{cp}$ element refers to the count of claims for which the practitioner p performed one or more services under the claim and the clinic c submitted the claim. The variable Number of Claims$_{c'p'}$ refers specifically to the number of claims for which p' performed one or more services and c' was the billing clinic.

In an embodiment, data retrieved from the PECOS undergoes some cleaning. In an embodiment, a modeled version of the PECOS data is used that replicates the enrollment data within PECOS verbatim. The modeled version of the PECOS data can be used rather than data stored in a relational database. In such an embodiment, a single table is created with single rows for all enrollment within dates of first and most recent observations. This single table can be created rather than the current raw form with one line per observation. In an embodiment, when an enrollment persists from one time period to the next, there is a row in each time period for that enrollment in the raw data.

In an embodiment, PECOS data is obtained via an application program interface (API) from a government-operated website. The results of these API queries are stored in a database table that stores a verbatim copy of the data alongside some information about when the API call was executed for the row.

In an embodiment, the practitioner-clinic 402 relationship is determined based on office carrier claims 402 for a practitioner 102 over a period of time. The practitioner-clinic relationship may be determined based on the last one year of data, the last five years of data, the last six months of data, and so forth. In an embodiment, the carrier claims 402 for the clinic 106 are analyzed to identify distinct performing clinic IDs 108 for each carrier claim 402. The carrier claim's line items are used to identify the performing practitioner ID 104. If a carrier claim's line items list multiple performing practitioner IDs 104, each distinct practitioner ID 104 is retained. The practitioner ID(s) 104 associated with the raw carrier claim 402 files may be joined back to the main claim information and the dataset may then be collapsed to extract a count of claims for each individual practitioner 102 billing under each clinic ID 108. These steps may be repeated for each time period of claims data available. The resulting metrics from the aforementioned analysis includes practitioner billing and clinic billing. The practitioner billing is the proportion of a practitioner's 102 total office claims billed to a specific clinic 106 (i.e. billed to the clinic ID 108 for that clinic 106). The clinic billing is the proportion of total office claims billed under a clinic performed by a given practitioner 102.

Figure 6:
FIG. 6 is a data flow chart for identifying and quantifying a practitioner-clinic enrollment relationship.

FIG. 6 is a schematic diagram of a method for identifying an enrollment relationship between practitioners 102 and clinics 106. The analysis described in connection with FIG. 6 can be used to determine under what clinic(s) 106 the practitioner 102 is enrolled. This is referred to as the practitioner-clinic enrollment 504 relationship.

In the United States, individuals and organizations participating in Medicare enroll in PECOS (Provider Enrollment and Chain/Ownership System). A practitioner 102 may enroll in PECOS using a practitioner ID 104, or the PECOS may assign and provide the practitioner ID 104 to the practitioner 102. In an embodiment, both may occur such that the enrolling practitioner 102 or other entity supplies an identification previously assigned through another process, and the PECOS assigns an enrollment ID. If the practitioner 102 is enrolling in PECOS for the first time, the practitioner 102 will also be assigned a PAC ID. Within the PECOS, the practitioner 102 may reassign billing rights under one or more clinics 106 also enrolled in the PECOS. The practitioner 102 enrolls under a clinic by associating the practitioner's 102 practitioner ID 104 with the appropriate clinic ID 108. This can be accomplished within the PECOS by assigning an enrollment ID to link the practitioner ID 104 with the IDs of other entities.

When a practitioner 102 is enrolled in PECOS, the practitioner ID 104 for that practitioner 102 is assigned a unique enrollment identification. The enrollment ID for the practitioner can be used to reassign billing rights to an organization enrollment. A reassignment constitutes an enrollment relationship between a practitioner 102 and an organization such as a clinic 106. Further in the Medicare systems in the United States, each clinic 106 is enrolled under a group ID 116. Because each clinic 106 is also enrolled under a group ID 116, the enrollment relationship between practitioners 102 and clinics 106 rolls up to groups 114 that are associated with group IDs 116. In an embodiment, some systems 118 are equivalent to some groups 114 as evidenced by the equality of their system IDs 120 and group IDs 116.

A practitioner 102 may reassign to multiple organization enrollments under different group IDs 116. In practice, these enrollments are sometimes retained after a practitioner transitions to a new practice or clinic 106. Because some enrollments may be "stale" and may no longer reflect the practitioner's 102 real-world associations, some enrollments may be discarded. Further, some enrollments may be used only infrequently. This may be the case when, for example, a practitioner 102 who reassigned rights to a specific clinic or group to have the ability to perform procedures for particular patients. In current Medicare systems in the United States, there is no information available on how frequently an enrollment relationship is used by a practitioner 102 other than through billing relationships as discussed in connection with FIG. 5. For this reason, enrollment relationships may be used only to roll clinic 106 locations up to groups 114 or systems 118 when necessary.

In an embodiment, an enrollment relationship between a practitioner 102 and a clinic 106 is identified by retrieving distinct practitioner ID 104 and clinic ID 108 relationships from enrollment and reassignment files in the PECOS over time. This analysis can result in determining a practitioner enrollment metric and a clinic enrollment metric. The practitioner enrollment metric identifies one or more clinics 106 at which a practitioner 102 in enrolled in Medicare in the United States. The clinic enrollment metric identifies one or more practitioners 102 that have enrolled in Medicare under a certain clinic 106.

Figure 7:
FIG. 7 is a data flow chart for identifying and quantifying clinic-group ownership relationship.

FIG. 7 is a schematic diagram of a data flow for analyzing ownership relationships between clinics 106 and groups 114. The analysis discussed in connection with FIG. 7 can be used to identify group(s) 114 that own one or more clinics 106. This is referred to as the clinic-group ownership 506. In the framework 100 described herein, clinics 106 are owned by groups 114. A group 114 is represented by a group ID 116. In some instances, the group ID 116 is a PAC ID (PECOS Associate Control ID) assigned by PECOS. In many cases, the clinic ID 108 associated with the clinic 106 appears in an enrollment file within PECOS for the group 114. Further within the enrollment file, the group 114 and the group ID 116 may be stated explicitly in connection with the clinic 106.

In some cases, the clinic ID 108 for a clinic 106 does not appear in PECOS enrollment 404 files in connection with a group 114, practitioner 102, or other entity. In these cases, group ID 116 may be imputed to the clinic 106 based on enrollment relationships 504 of practitioners 102 associated with the clinic 106 by the billing relationship 502. Analysis of the enrollment relationships 504 between practitioners 102 and clinics 106 is discussed in further detail in connection with FIG. 6.

Enrollment Proportion Method (used if no direct enrollment between clinic 106 and any group 116 exists):

$$\text{Ownership1}_{G'c'} = \text{TRUE if } \frac{\sum_{c \in G'} \sum_{p \in P_{c'c}} \text{Practitioner Billing}_{pc'c}}{\sum_{p \in P_{c'}} \text{Practitioner Billing}_{pc'}} > 0.5,$$

$$\text{otherwise FALSE Note}: c' \notin G'$$

Squared Enrollment Proportion Method (used if no direct enrollment between clinic 106 and any group 116 exists and all $\text{Ownership}_{g'c'}$ from the Enrollment Proportion Method [see the following equation] for clinic c' equal FALSE):

$$\text{Ownership2}_{G'c'} = \text{TRUE if } \frac{(\text{Ownership1}_{G'c'})^2}{\sum_{G \in \mathbb{G}_{c'}} (\text{Ownership1}_{Gc'})^2} > 0.5,$$

$$\text{otherwise FALSE Note}: c' \notin G'$$

Under both methods, $$\text{Ownership Confidence}_{G'c'} =$$

$$\frac{\sum_{c \in G'} \sum_{p \in P_{c'c}} \text{Practitioner Billing}_{pc'c}}{\sum_{p \in P_{c'}} \text{Practitioner Billing}_{pc'}} \text{ if Ownership1}_{G'c'} =$$

$$\text{TRUE or Ownership2}_{G'c'} = \text{TRUE. Note}: c' \notin G'$$

In the equations above, c' is the clinic being referenced by the final metric, G' is the group being referenced by the final metric and is a set of clinics enrolled under the group, $P_{c'}$ is the set of all practitioners who billed services under clinic c', $P_{c'c}$ is the set of all practitioners in $P_{c'}$ who also enrolled under any clinic c that is an element of G', and $\mathbb{G}_{c'}$ is the set of groups with any enrolled providers billing under clinic c'. Note that c' is not an element of G'. Thus, $P_{c'}$ specifically references the practitioners p with non-zero Practitioner Billing$_{pc'}$ scores. The Practitioner Billing scores referenced are calculated previously as described above in connection with the Enrollment Proportion Method discussed in relation to FIG. 6, where G' is an element of $\mathbb{G}_{c'}$.

It should be noted that although clinics may technically be enrolled under more than group and in fairly rare cases are actually enrolled under more than one group), the imputation methods executed in these formulas and the order in which they are invoked constrain the number of group owners of a clinic to a maximum of one. That is, there will be no clinic c' for which more than one Ownership$_{Gc'}$ result equals TRUE. It is also possible that imputation can fail, in which case other methods not yet developed may be employed, but for now the clinic will not have any group ownership relationship in the analysis (whatever the underlying, yet unrecognized reality may be).

In an embodiment, practitioners 102 are professionally associated with a clinic 106. This could mean the practitioners 102 are employed by the clinic 106, bill carrier claims 402 under the clinic 106, are in a partnership with other practitioners 102 in the clinic 106, and so forth. When the clinic ID 108 for a clinic 106 does not appear within an enrollment database, such as the PECOS enrollment 404 database, the practitioners 102 are linked to the clinic 106 by way of the billing relationship 502. In an embodiment, if more than 50% of the practitioners 102 (weighted by the provider billing relationship metric defined above) who are professionally associated with the clinic 106 by way of the billing relationship 502 enroll under a certain group ID 116, that group ID 116 can be imputed to the clinic 106, with the weighted percentage serving as a measure of the certainty of the ownership relationship 506 so imputed. In such an instance, the group ID 116 is imputed to the clinic ID 108 within the enrollment database. In an alternative embodiment, in which no group ID 116 accounts for more than 50% of the enrollments of the practitioners 102 linked to the clinic 106, the group ID 116 is imputed to the clinic ID 108 if the squared proportion of provider enrollments under the group ID 116 exceeds 50% of the sum of the squared proportions of all enrollments for the practitioners 102 associated with the clinic 106. In some instances, these cases have a perfect ownership relationship wherein each of the practitioners 102 reassign to the same group ID 116. In some cases, the clinic 106 has a less than perfect ownership when the group ID 116 is imputed to the clinic 106.

In an embodiment, the clinic-group ownership 506 is determined based on carrier claims 402 and PECOS enrollment 404 data. In some cases, the clinic ID 108 for the clinic 106 is identified based on clinic enrollment to retrieve the group ID 116. Where no enrollment exists for the clinic 106, a method includes using reassignments indicated in the PECOS enrollment 404 database. In such an instance, a group ID 116 is imputed to the clinic 106 based on the reassignment files of the practitioners 102 that are professionally associated with the clinic 106. In an embodiment, the reassigned group IDs 116 for practitioners 102 billing carrier claims 402 under a clinic ID 108 are identified using the enrollment and reassignment files. The proportion of all clinic ID 108 and group ID 116 combinations represented by each combination are calculated. The proportions may be weighted by the practitioner's 102 billing relationships and by the number of claims a practitioner 102 bills at the clinic 106. The level of concentration each practitioner 102 shares with each clinic ID 108 is calculated by taking the sum of the squared proportions.

In an embodiment, a certain group ID 116 and practitioner ID 104 combination is selected if the combination has more than 50% of the reassignments of the clinic's 106 practitioners 102. This can be determined by using the enrollment and reassignment files to identify the reassigned group IDs 116 of practitioners 102 (the enrollment relationships 504 of the practitioners) who bill carrier claims 402 under a clinic ID 108, as evidenced by a previously determined billing relationship 502 between the provider 102 and the clinic 106.

In an embodiment a certain group ID 116 and practitioner ID 104 combination is selected if the combination has a squared proportion greater than 50% of the concentration of a practitioner's 102 shares within the clinic 106. This can be calculated by taking the sum of the squared proportions as done for example in the Herfindahl-Hirschman Index of market concentration.

$$\text{Practitioner Group Billing}_{Gp'} = \frac{\sum_{c \in G} \text{Number of Claims}_{p'c}}{\sum_{c \in C_{p'}} \text{Number of Claims}_{p'c}}$$

$$\text{Group Billing}_{Gp'} = \frac{\sum_{c \in G} \text{Number of Claims}_{p'c}}{\sum_{c \in G} \sum_{p \in P_c} \text{Number of Claims}_{pc}}$$

In the equations above, G is the group being referenced by the final metric and is a set of all clinics enrolled under the group, p' is the practitioner being referenced by the final metric, $C_{p'}$ is the set of all clinics under which practitioner p' bills, and $P_c$ is the set of all practitioners billing claims under a clinic c in group G. A Number of Claims$_{pc}$ element refers to the count of claims for which the practitioner p performed one or more services under the claim and the clinic c submitted the claim.

The metrics which can be derived from the clinic-group ownership 506, in connection with the practitioner-clinic billing relationships 502, include practitioner group billing and group billing. The practitioner group billing is the proportion of the practitioner's office claims billed under any of a group's 114 clinics 106. The group billing is the proportion of all office claims billed under any of the group's 114 clinics 106 that were performed by a specific practitioner 102.

Figure 8:
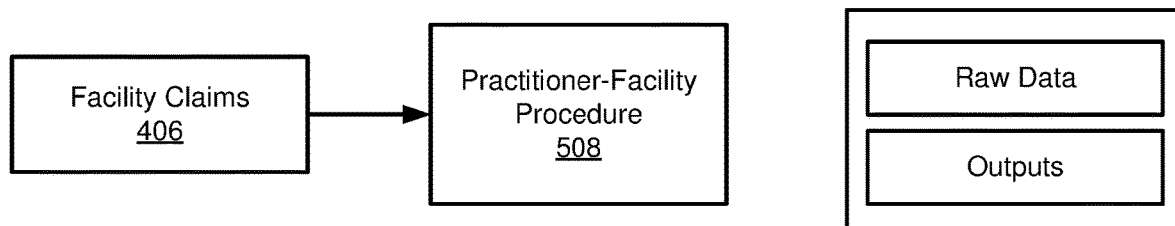
FIG. 8 is a data flow chart for identifying and quantifying a practitioner-facility procedure relationship.

FIG. 8 is a schematic diagram of a data flow for identifying and quantifying the practitioner-facility relationship with respect to procedures. The analysis discussed in connection with FIG. 8 can be used to determine at what facilities 110 a practitioner 102 is performing procedures. This is referred to as the practitioner-facility procedures 508 metric.

$$\text{Practitioner Facility Procedure}_{p'f'} = \frac{\text{Number of Claims}_{p'f'}}{\sum_{f \in F_{p'}} \text{Number of Claims}_{p'f}}$$

$$\text{Facility Procedure}_{p'f'} = \frac{\text{Number of Claims}_{p'f'}}{\sum_{p \in P_{f'}} \text{Number of Claims}_{pf'}}$$

In the equations above, p' is the practitioner being referenced by the final metric, f is the facility being referenced by the final metric, $F_{p'}$ is the set of all facilities f (including f') at which the practitioner p' performed one or more procedures, and $P_{f'}$ is the set of all practitioners p (including p') who performed one or more procedures at facility f'. A Number of Claims$_{pf}$ element refers to the count of facility claims for which the practitioner p performed one or more procedures under the claim and the facility f that submitted the facility claim. Number of Claims$_{p'f'}$ therefore refers specifically to the number of facility claims for which p' performed one or more procedures at facility f'.

When a practitioner 102 performs a procedure at a facility 110, a facility claim 406 is submitted by the facility 110. The facility claim 406 includes the one or more practitioner IDs 104 for the one or more practitioners 102 involved in the procedure, service, device, pharmaceutical, and so forth provided at the facility 110. The facility claim 406 may include the facility ID 112 associated with the facility 110. In some instances, the facility ID 116 is a CMS Certification Number (CCN) or a CMS Provider Number. The proportion of procedures performed by a practitioner 102 at a certain facility 110 is quantified based on the relationship in the facility claims 406 between practitioner IDs 104 and facility IDs 112. Further, the proportion of the facility's 110 procedure volume that was performed by a certain practitioner 102 is quantified based on the relationship in the facility claims 406 between practitioner IDs 104 and facility IDs 112. These procedure volumes provide a link between practitioners 102 and facilities 110 apart from any official ownership or employment relationships.

The raw data input includes all facility claims files such as inpatient, outpatient, hospice, and so forth. The practitioner-facility procedure 508 is determined by identifying the distinct practitioner IDs 104 that participated in each facility claim 406. This can be performed for each claim in a given year. Participating practitioner IDs 104 are in the attending, operating, rendering, and other practitioner fields. A practitioner ID 104 can appear in more than one of these fields and the duplicates should be handled when calculating the practitioner-facility procedures 508 metric. For each pair including a participating practitioner ID 104 and a facility ID 112, the number of facility claims 406 represented by the pair is counted. The facility claim 406 numbers by distinct pair are summed across all facility claim 406 files. This process may be repeated for each year of available claims data.

The practitioner-facility procedures 508 metrics results in a practitioner-facility procedure volume metric and a facility procedure volume metric. The practitioner-facility procedure volume metric is the proportion of a practitioner's 102 total procedure claims performed at a certain facility 110. A practitioner's 102 procedure claim is a claim in which the practitioner 102 participated in the procedure. The facility 110 procedure volume is the proportion of procedures performed at a certain facility 110 by each of one or more practitioners 102 using the certain facility 110.

Figure 9:
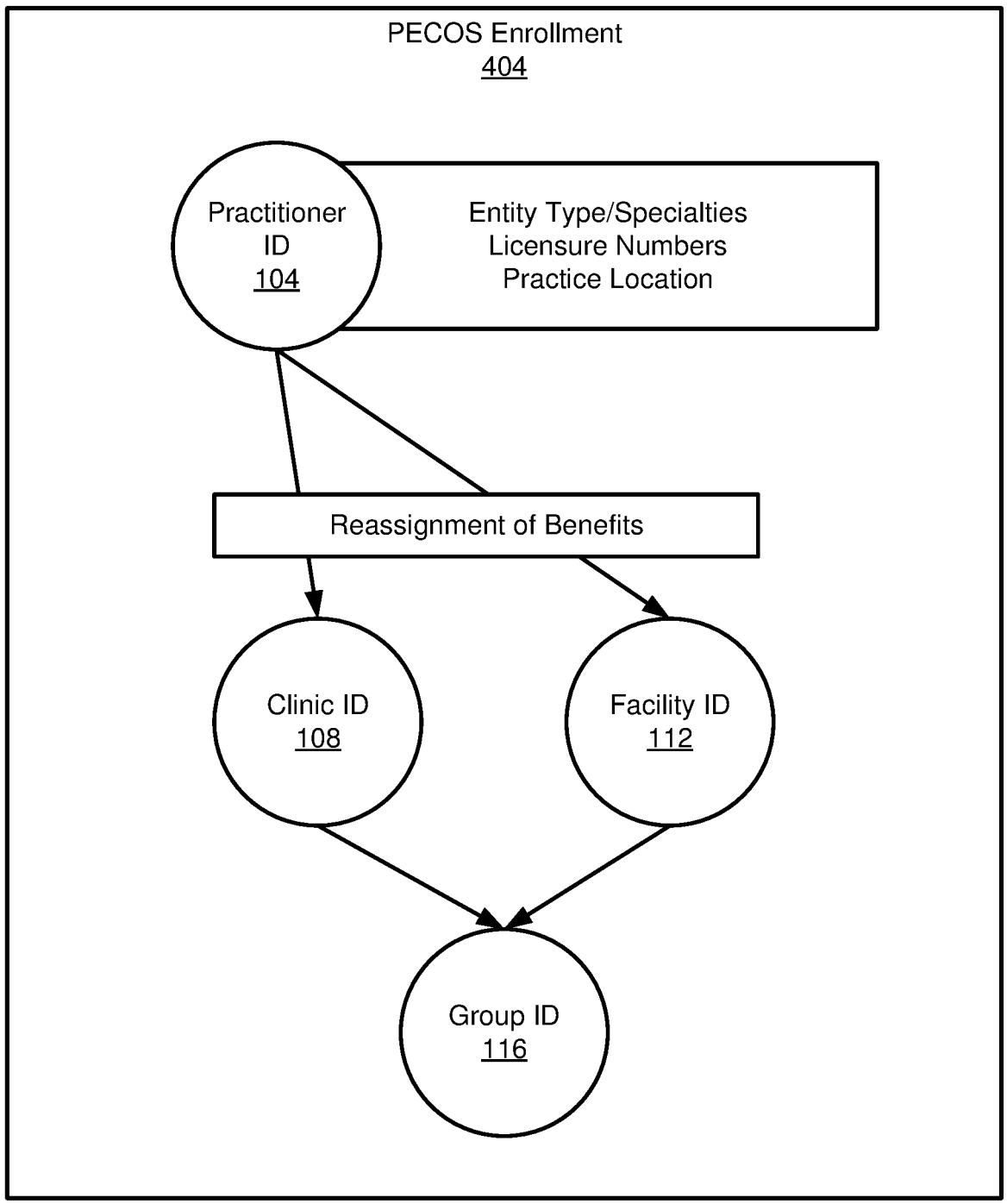
FIG. 9 is a schematic diagram of data relationships within a PECOS enrollment file.

FIG. 9 is a schematic diagram of a PECOS enrollment 404 information relationship. In the United States, the PECOS is used to track the status of healthcare practitioners, and the relationships those healthcare practitioners have with other entities, such as clinics 106, facilities 110, and groups 114. In the PECOS, a practitioner 102, clinic 106, or facility 110 provides a practitioner ID 104, clinic ID 108, or facility ID 112 in the form of an NPI. Additionally, each such enrolling individual or entity is assigned a PECOS Associate Control ID, or PAC ID, and each unique enrollment is assigned an enrollment ID. Multiple clinics 106 and/or facilities 110 may enroll under a common PAC ID, which serves as a group ID 116 identifying a group 114 when one or more clinics 108 enrolls under the PAC ID, and also as a system ID 120 identifying a system 118 when one or more facilities 110 enrolls under the PAC ID.

Within PECOS, a practitioner 102 can assign rights to bill claims for Medicare services in his or her behalf to another entity, such as a clinic 106, facility 110, and/or other practitioner 102 by storing a reassignment file that links the reassigning practitioner's 102 practitioner ID 104 to the clinic ID 108, the facility ID 112, and/or other practitioner 102, as applicable. This reassignment of benefits is an indication that the practitioner 102 is professionally associated with a clinic 106, facility 110, and/or practitioner 102. A reassignment by a practitioner 102 to a clinic 106 or facility 110 under a group 114 allows for further identification of a relationship between the practitioner 102 and the group 114.

In an example, a practitioner is an emergency medicine physician employed by a hospital. The physician is enrolled in PECOS and supplies an individual NPI. Additionally, the hospital is enrolled in PECOS as a facility and provides an NPI. The physician may indicate within PECOS that the physician has assigned rights to the hospital, or that the physician is otherwise associated with the hospital.

In a further example, a practitioner is a family medicine physician operating as a sole proprietor. The practitioner submits carrier claims to patients on his own and does not operate through another entity. However, the family medicine physician, despite being a sole proprietor, is professionally associated with a clinic. The family medicine physician may be a partner in a family medicine clinical practice, for example. The family medicine physician may enroll in PECOS as a sole proprietor and may further indicate a relationship with the clinic.

The PECOS enrollment 404 information is not always accurate. The enrollment information within PECOS is often stale with respect to real-world relationships. For example, a practitioner may transition from being employed by a hospital to operating as a sole proprietor. This change is reflected in PECOS only if the practitioner or some other entity indicates within PECOS that the change has occurred. In such an instance, PECOS is not reliable to indicate the real-world professional relationships for that practitioner. In such an instance, the carrier claims submitted by the practitioner can be analyzed in lieu of the information in PECOS, and the analysis gleaned from the carrier claims can be used to override the information in PECOS to identify the practitioner's real-world relationships.

In an embodiment, data received from PECOS includes four tables, including a base enrollment table, a reassignment table, an address table, and a secondary specialty table. The base enrollment table includes one row per active enrollment at the time of viewing the table for all individuals and entities enrolled in the Medicare system. The enrollment IDs define unique identifiers for the rows. Practitioner IDs 104, organization IDs 108, PAC IDs, names, states, and specialty/facility categories may be included the base enrollment table. A single entity or individual may be identified by a PAC ID or NPI and may have more than one enrollment, and therefore may have more than one enrollment ID. This is very common for different entities with different NPIs enrolled under a common PAC ID. In an embodiment, individuals only have one PAC ID assigned directly. Individuals can be distinguished from entities by the first character of the enrollment ID (i.e. I for individuals and O for organizations or entities).

The reassignment table includes reassignments of billing rights from one enrollment to another. Typically, the enrollment receiving the reassignment is an entity, but this is not always the case. All those that designate reassignments are individual practitioners 102, though not all practitioners 102 in the base enrollment file reassign billing rights. The reassignment table includes two columns, including an enrollment ID of the assigning enrollment, and an enrollment ID of the enrollment receiving the reassignment.

The address table includes the city, state, and zip code for enrollments tied back to the base enrollment table based on enrollment IDs. In an embodiment, there are more than one address per enrollment.

The secondary specialty table includes specialty information that might not apply in each case. It is possible for an enrollment to be associated with multiple specialty types and facility types. These cases are reflected in the secondary specialty table and linked back to the base enrollment table based on enrollment IDs.

Figure 10:
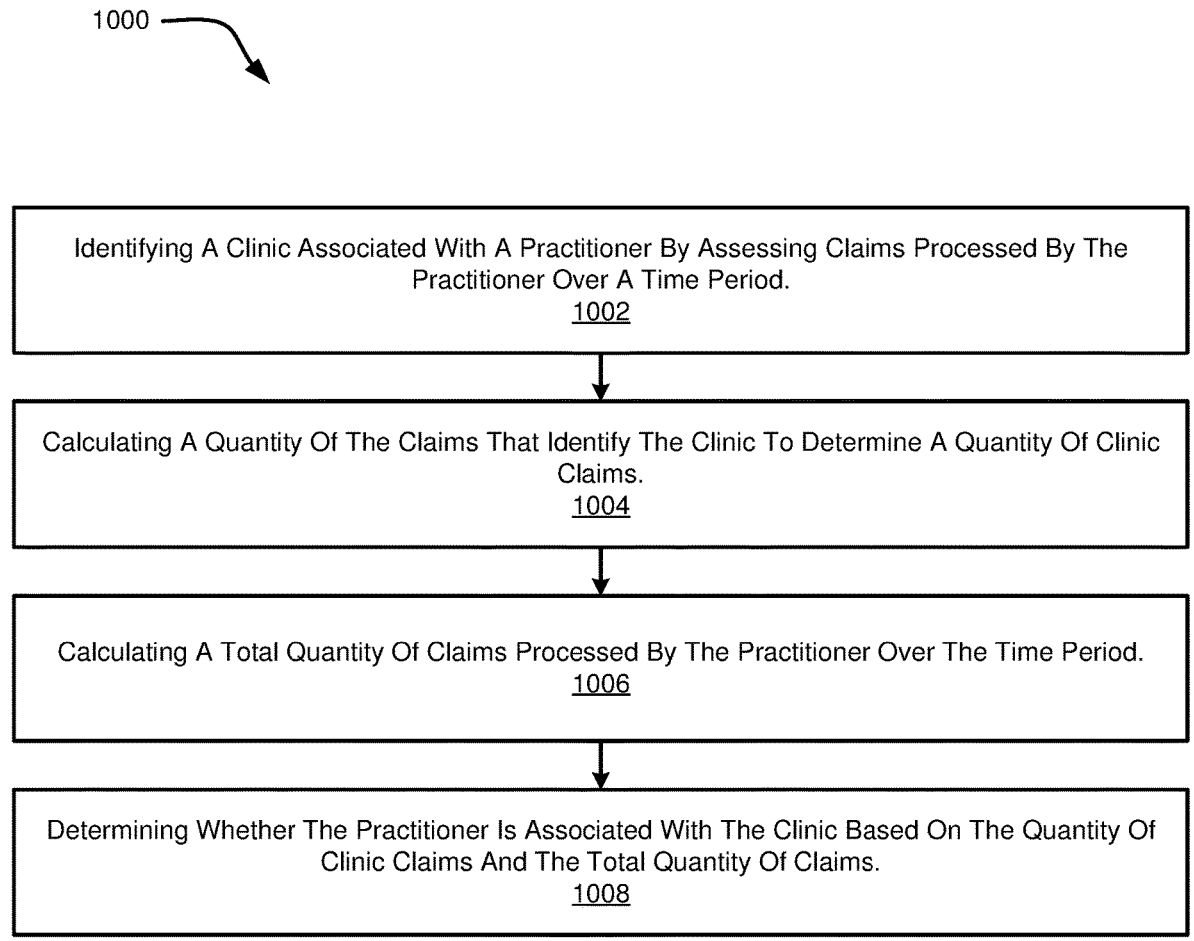
FIG. 10 is a schematic flow chart diagram of a method for identifying relationships between healthcare practitioners and healthcare clinics based on billed claims.

FIG. 10 is a schematic flow chart diagram of a method 1000 for identifying relationships between healthcare practitioners and healthcare clinics based on billed claims. The method 1000 may be performed by a computing resource configurable to execute instructions stored in non-transitory computer readable storage media.

The method 1000 begins and a computing resource identifies at 1002 a clinic associated with a practitioner by assessing claims processed by the practitioner over a time period. The method 1000 continues and a computing resource calculates at 1004 a quantity of the claims that identify the clinic to determine a quantity of clinic claims. The method 1000 includes calculating at 1006 a total quantity of claims processed by the practitioner over the time period. The method 1000 includes determining at 1008 whether the practitioner is associated with the clinic based on the quantity of clinic claims and the total quantity of claims.

Figure 11:
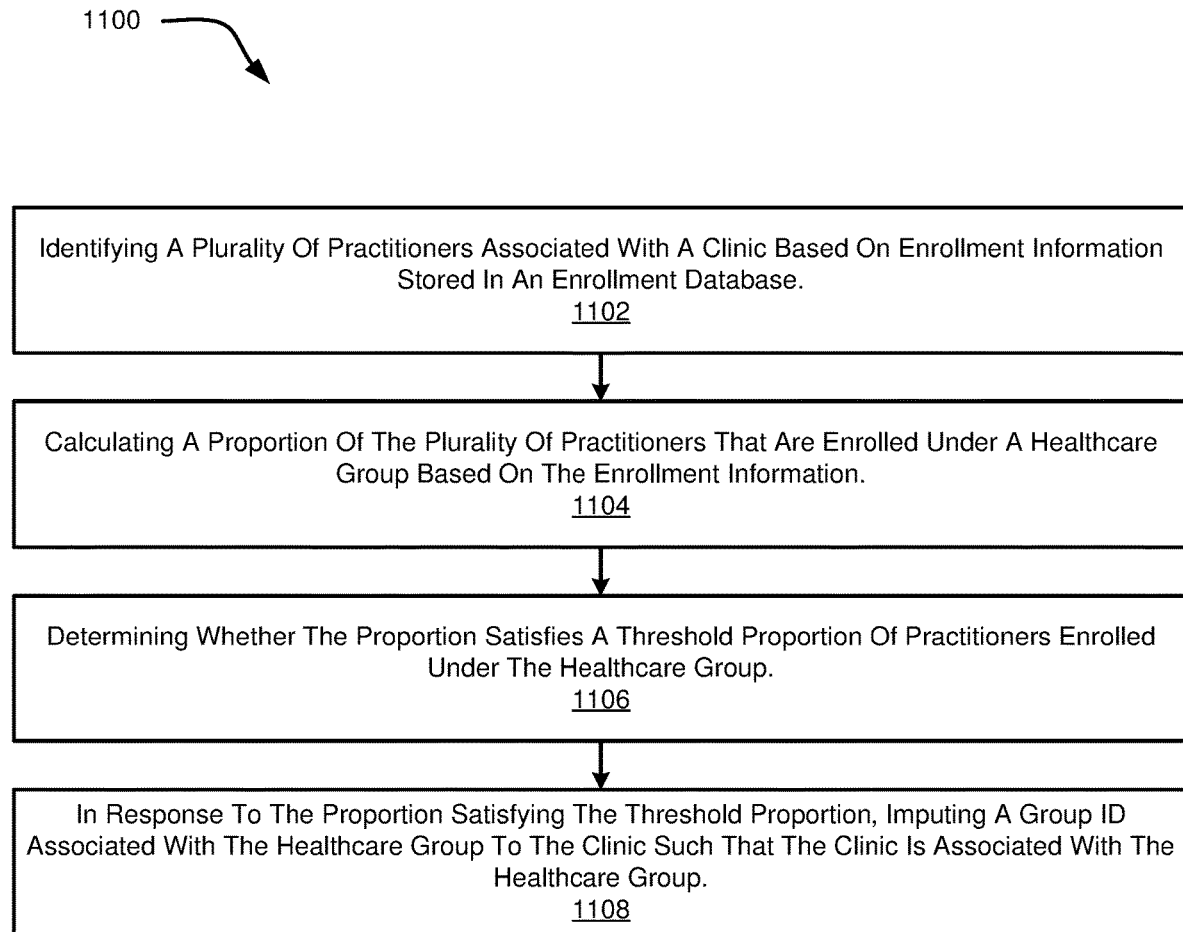
FIG. 11 is a schematic flow chart diagram of a method for imputing a group ID to a clinic based on enrollment information stored in an enrollment database.

FIG. 11 is a schematic flow chart diagram of a method 1100 for imputing a group ID to a clinic based on enrollment information. The method 1100 may be performed by a computing resource configurable to execute instructions stored in non-transitory computer readable storage media.

The method 1100 begins and a computing resource identifies at 1102 a plurality of practitioners associated with a clinic based on enrollment information stored in an enrollment database. The method 1100 includes calculating at 1104 a proportion of the plurality of practitioners that are enrolled under a healthcare group based on the enrollment information. The method 1100 includes determining at 1106 whether the proportion satisfies a threshold proportion of practitioners enrolled under the healthcare group. The method 1100 includes, in response to the proportion satisfying the threshold proportion, imputing at 1108 a group ID associated with the healthcare group to the clinic such that the clinic is associated with the healthcare group.

Figure 12:
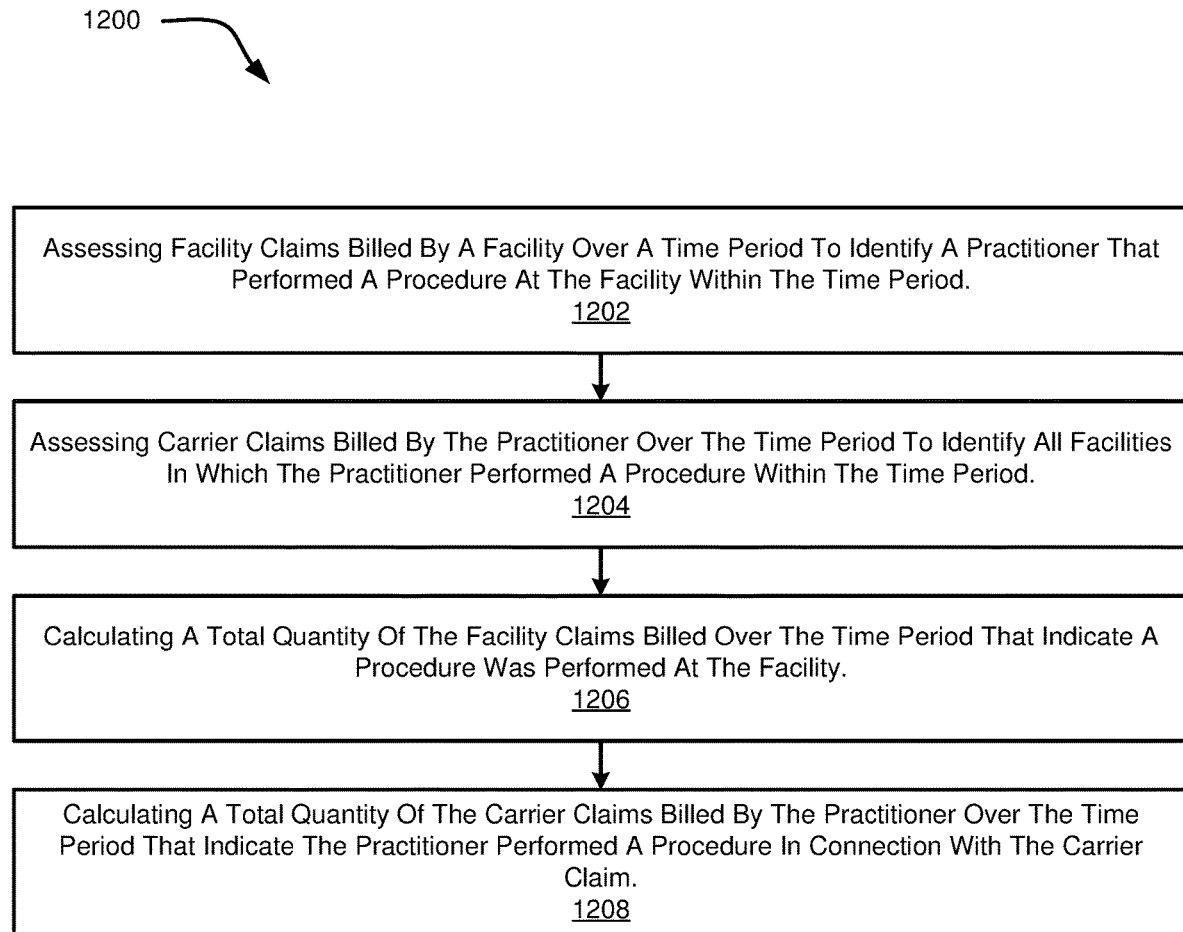
FIG. 12 is a schematic flow chart diagram of a method for identifying procedure relationships between healthcare facilities and healthcare practitioners based on billed claims.

FIG. 12 is a schematic flow chart diagram of a method 1200 for identifying and quantifying procedure relationships between healthcare facilities and healthcare practitioners based on billed claims. The method 1200 may be performed by a computing resource configurable to execute instructions stored in non-transitory computer readable storage media.

The method 1200 begins and a computing resource assesses at 1202 facility claims billed by a facility over a time period to identify a practitioner that performed a procedure at the facility within the time period. The method 1200 includes assessing at 1204 carrier claims billed by the practitioner over the time period to identify all facilities in which the practitioner performed a procedure within the time period. The method 1200 includes calculating at 1206 a total quantity of the facility claims billed over the time period that indicate a procedure was performed at the facility. The method 1200 includes calculating at 1208 a total quantity of the carrier claims billed by the practitioner over the time period that indicate the practitioner performed a procedure in connection with the carrier claim.

Figure 13:
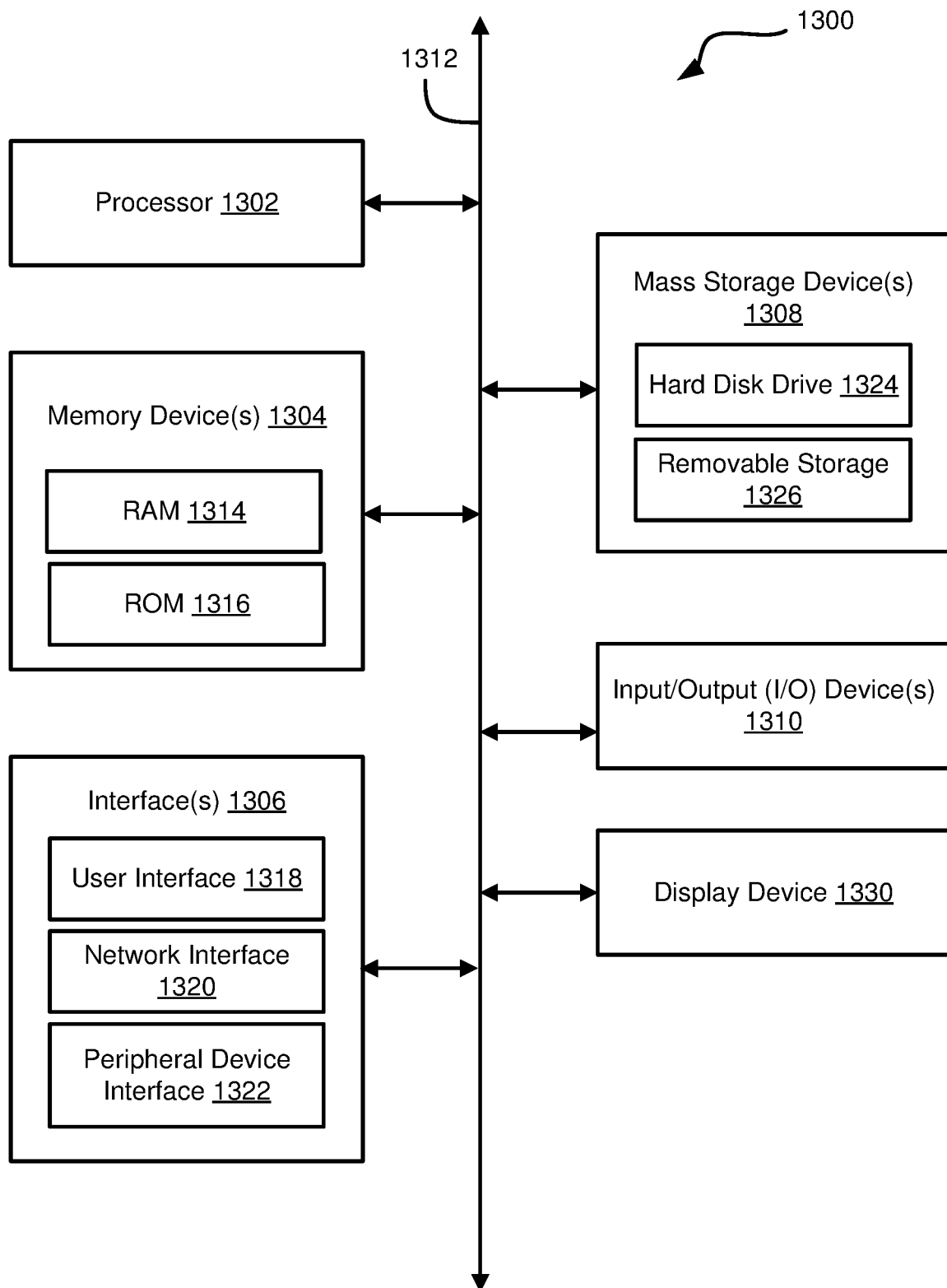
FIG. 13 is a schematic diagram illustrating components of an example computing device.

Referring now to FIG. 13, a block diagram of an example computing device 1300 is illustrated. Computing device 1300 may be used to perform various procedures, such as those discussed herein. Computing device 1300 can perform various monitoring functions as discussed herein, and can execute one or more application programs, such as the application programs or functionality described herein. Computing device 1300 can be any of a wide variety of computing devices, such as a desktop computer, in-dash computer, vehicle control system, a notebook computer, a server computer, a handheld computer, tablet computer and the like.

Computing device 1300 includes one or more processor(s) 1304, one or more memory device(s) 1304, one or more interface(s) 1306, one or more mass storage device(s) 1308, one or more Input/output (I/O) device(s) 1110, and a display device 1330 all of which are coupled to a bus 1312. Processor(s) 1304 include one or more processors or controllers that execute instructions stored in memory device(s) 1304 and/or mass storage device(s) 1308. Processor(s) 1304 may also include various types of computer-readable media, such as cache memory.

Memory device(s) 1304 include various computer-readable media, such as volatile memory (e.g., random access memory (RAM) 1314) and/or nonvolatile memory (e.g., read-only memory (ROM) 1316). Memory device(s) 1304 may also include rewritable ROM, such as Flash memory.

Mass storage device(s) 1308 include various computer readable media, such as magnetic tapes, magnetic disks, optical disks, solid-state memory (e.g., Flash memory), and so forth. As shown in FIG. 13, a particular mass storage device 1308 is a hard disk drive 1324. Various drives may also be included in mass storage device(s) 1308 to enable reading from and/or writing to the various computer readable media. Mass storage device(s) 1308 include removable media 1326 and/or non-removable media.

I/O device(s) 1310 include various devices that allow data and/or other information to be input to or retrieved from computing device 1300. Example I/O device(s) 1310 include cursor control devices, keyboards, keypads, microphones, monitors or other display devices, speakers, printers, network interface cards, modems, and the like.

Display device 1330 includes any type of device capable of displaying information to one or more users of computing device 1300. Examples of display device 1330 include a monitor, display terminal, video projection device, and the like.

Interface(s) 1306 include various interfaces that allow computing device 1300 to interact with other systems, devices, or computing environments. Example interface(s) 1306 may include any number of different network interfaces 1320, such as interfaces to local area networks (LANs), wide area networks (WANs), wireless networks, and the Internet. Other interface(s) include user interface 1318 and peripheral device interface 1322. The interface(s) 1306 may also include one or more user interface elements 1318. The interface(s) 1306 may also include one or more peripheral interfaces such as interfaces for printers, pointing devices (mice, track pad, or any suitable user interface now known to those of ordinary skill in the field, or later discovered), keyboards, and the like.

Bus 1312 allows processor(s) 1304, memory device(s) 1304, interface(s) 1306, mass storage device(s) 1308, and I/O device(s) 1310 to communicate with one another, as well as other devices or components coupled to bus 1312. Bus 1312 represents one or more of several types of bus structures, such as a system bus, PCI bus, IEEE bus, USB bus, and so forth.

EXAMPLES

The following examples pertain to further embodiments.

Example 1 is a method for identifying relationships between healthcare practitioners and healthcare clinics based on billed claims. The method includes identifying a clinic associated with a practitioner by assessing claims processed by the practitioner over a time period. The method includes calculating a quantity of the claims that identify the clinic to determine a quantity of clinic claims. The method includes calculating a total quantity of claims processed by the practitioner over the time period. The method includes determining whether the practitioner is associated with the clinic based on the quantity of clinic claims and the total quantity of claims.

Example 2 is a method as in Example 1, further comprising: identifying a practitioner ID associated with the practitioner; identifying a clinic ID associated with the clinic; and reading an enrollment database to determine whether the practitioner ID is assigned to the clinic ID.

Example 3 is a method as in any of Examples 1-2, further comprising determining the likelihood the practitioner is a member of the clinic based on: the quantity of clinic claims identifying the clinic; the total quantity of claims processed by the practitioner; and whether the practitioner ID is assigned to the clinic ID within the enrollment database.

Example 4 is a method as in any of Examples 1-3, further comprising determining whether enrollment information for the practitioner and/or the clinic within the enrollment database is stale with respect to real-world associations based on: the quantity of clinic claims identifying the clinic; the total quantity of claims processed by the practitioner; and whether the practitioner ID is assigned to the clinic ID within the enrollment database.

Example 5 is a method as in any of Examples 1-4, wherein: the practitioner ID is an individual National Provider Identifier (NPI); the clinic ID is an organization NPI; and the enrollment database is a database associated with Provider Enrollment, Chain and Ownership System (PECOS).

Example 6 is a method as in any of Examples 1-5, wherein the claims processed by the practitioner over the time period are carrier claims, and wherein identifying the clinic associated with the practitioner comprises reading the carrier claims to identify one or more distinct clinic IDs noted in the carrier claims.

Example 7 is a method as in any of Examples 1-6, wherein the claims processed by the practitioner over the time period are carrier claims, and wherein calculating the quantity of clinic claims identifying the clinic comprises reading the carrier claims and counting a quantity of the carrier claims that include a clinic ID associated with the clinic.

Example 8 is a method as in any of Examples 1-7, further comprising calculating a clinic proportion by calculating the total number of claims processed by the practitioner that include a clinic ID associated with the clinic, and wherein quantifying the relationship between the practitioner and the clinic comprises quantifying based on the clinic proportion.

Example 9 is a method as in any of Examples 1-8, further comprising: determining whether the clinic proportion meets a threshold; and in response to the clinic proportion meeting the threshold, determining that the practitioner is professionally associated with the clinic.

Example 10 is a method as in any of Examples 1-9, further comprising: in response to the clinic proportion meeting the threshold, determining whether the practitioner is assigned to the clinic within an enrollment database; and determining whether data for the practitioner in the enrollment database is stale with respect to the practitioner's real-world association with the clinic.

Example 11 is one or more processors configurable to execute instructions stored in non-transitory computer readable storage media. The instructions include identifying a clinic associated with a practitioner by assessing claims processed by the practitioner over a time period. The instructions include calculating a quantity of the claims that identify the clinic to determine a quantity of clinic claims. The instructions include calculating a total quantity of claims processed by the practitioner over the time period. The instructions include determining whether the practitioner is associated with the clinic based on the quantity of clinic claims and the total quantity of claims.

Example 12 is one or more processors as in Example 11, wherein the instructions further comprise: identifying a practitioner ID associated with the practitioner; identifying a clinic ID associated with the clinic; and reading an enrollment database to determine whether the practitioner ID is assigned to the clinic ID.

Example 13 is one or more processors as in any of Examples 11-12, wherein the instructions further comprise determining the likelihood the practitioner is a member of the clinic based on: the quantity of clinic claims identifying the clinic; the total quantity of claims processed by the practitioner; and whether the practitioner ID is assigned to the clinic ID within the enrollment database.

Example 14 is one or more processors as in any of Examples 11-13, further comprising determining whether enrollment information for the practitioner and/or the clinic within the enrollment database is stale with respect to real-world associations based on: the quantity of clinic claims identifying the clinic; the total quantity of claims processed by the practitioner; and whether the practitioner ID is assigned to the clinic ID within the enrollment database.

Example 15 is one or more processors as in any of Examples 11-14, wherein: the practitioner ID is an individual National Provider Identifier (NPI); the clinic ID is an organization NPI; and the enrollment database is a database associated with Provider Enrollment, Chain and Ownership System (PECOS).

Example 16 is one or more processors as in any of Examples 11-15, wherein the claims processed by the practitioner over the time period are carrier claims, and wherein identifying the clinic associated with the practitioner comprises reading the carrier claims to identify one or more distinct clinic IDs noted in the carrier claims.

Example 17 is one or more processors as in any of Examples 11-16, wherein the claims processed by the practitioner over the time period are carrier claims, and wherein calculating the quantity of clinic claims identifying the clinic comprises reading the carrier claims and counting a quantity of the carrier claims that include a clinic ID associated with the clinic.

Example 18 is one or more processors as in any of Examples 11-17, further comprising calculating a clinic proportion by calculating the total number of claims processed by the practitioner that include a clinic ID associated with the clinic, and wherein quantifying the relationship between the practitioner and the clinic comprises quantifying based on the clinic proportion.

Example 19 is one or more processors as in any of Examples 11-18, further comprising: determining whether the clinic proportion meets a threshold; and in response to the clinic proportion meeting the threshold, determining that the practitioner is professionally associated with the clinic.

Example 20 is one or more processors as in any of Examples 11-19, further comprising: in response to the clinic proportion meeting the threshold, determining whether the practitioner is assigned to the clinic within an enrollment database; and determining whether data for the practitioner in the enrollment database is stale with respect to the practitioner's real-world association with the clinic.

Example 21 is a method for imputing a group ID to a clinic based on enrollment information. The method includes identifying a plurality of practitioners associated with a clinic based on enrollment information stored in an enrollment database. The method includes calculating a proportion of the plurality of practitioners that are enrolled under a healthcare group based on the enrollment information. The method includes determining whether the proportion satisfies a threshold proportion of practitioners enrolled under the healthcare group. The method includes in response to the proportion satisfying the threshold proportion, imputing a group ID associated with the healthcare group to the clinic such that the clinic is associated with the healthcare group.

Example 22 is a method as in Example 21, wherein the clinic is a single identified clinics and the healthcare group is a single identified healthcare group.

Example 23 is a method as in any of Examples 21-22, wherein, for each of the plurality of practitioners, identifying whether a practitioner is associated with the clinic comprises: assessing office claims processed by the practitioner over a time period; calculating a total quantity of office claims processed by the practitioner over the time period; calculating a proportion of the total quantity of office claims that identify the clinic; and determining whether the practitioner is associated with the clinic based on whether the proportion of the total quantity of office claims meets a threshold.

Example 24 is a method as in any of Examples 21-23, wherein, for each of the plurality of practitioners, identifying whether a practitioner is associated with the clinic comprises determining whether the practitioner has designated an assignment file to the clinic within the enrollment database.

Example 25 is a method as in any of Examples 21-24, wherein: each practitioner listed in the enrollment database comprises a unique practitioner ID; each clinic listed in the enrollment database comprises a unique clinic ID; and each healthcare group listed in the enrollment database comprises a unique group ID.

Example 26 is a method as in any of Examples 21-25, wherein: identifying whether a practitioner of the plurality of practitioners is associated with the clinic comprises determining based at least in part on the enrollment information and whether the applicable practitioner ID is enrolled under the clinic ID of the clinic; and the method further comprises determining which of the plurality of practitioners is enrolled under the healthcare group based on whether the applicable practitioner ID is associated with the group ID of the healthcare group.

Example 27 is a method as in any of Examples 21-26, wherein: the practitioner ID is an individual National Provider Identifier (NPI); the clinic ID is an organization NPI; the group ID is a PECOS Associate Control ID (PAC ID) assigned by Provider Enrollment, Chain and Ownership System (PECOS); and the enrollment database is a database associated with the PECOS.

Example 28 is a method as in any of Examples 21-27, wherein the threshold proportion is 50% such that the group ID of the healthcare group is imputed to the clinic if 50% or more of the plurality of practitioners associated with the clinic are enrolled under the healthcare group within the enrollment database.

Example 29 is a method as in any of Examples 21-28, wherein the threshold proportion indicates that the group ID of the healthcare group should be imputed to the clinic if a squared proportion of the plurality of practitioners that are enrolled under the healthcare group exceeds 50% of a sum of squared proportions of all group enrollments across multiple different healthcare groups for the plurality of practitioners associated with the clinic.

Example 30 is a method as in any of Examples 21-29, further comprising, in response to imputing the group ID associated with the healthcare group to the clinic, determining whether the healthcare group has perfect ownership of the clinic such that each of the plurality of practitioner associated with the clinic is enrolled under the healthcare group within the enrollment database.

Example 31 is a method for identifying relationships between healthcare practitioners and healthcare facilities based on billed claims. The method includes assessing facility claims billed by a facility over a time period to identify a practitioner that performed a procedure at the facility within the time period. The method includes assessing carrier claims billed by the practitioner over the time period to identify all facilities in which the practitioner performed a procedure within the time period. The method includes calculating a total quantity of the facility claims billed over the time period that indicate a procedure was performed at the facility. The method includes calculating a total quantity of the carrier claims billed by the practitioner over the time period that indicate the practitioner performed a procedure.

Example 32 is a method as in Example 31, wherein the practitioner is a single identified practitioner and the facility is a single identified facility, and wherein a plurality of practitioners provide care at the facility and the practitioner provides care at one or more facilities.

Example 33 is a method as in any of Examples 31-32, further comprising calculating a facility procedure volume metric indicating a proportion of the facility's procedure volume that was provided by the practitioner over the time period based on the total quantity of the facility claims that indicate a procedure was performed at the facility and a quantity of the facility claims that identify the practitioner performed a procedure at the facility.

Example 34 is a method as in any of Examples 31-33, further comprising determining whether the practitioner and the facility are in a professional relationship apart from an official ownership or employment relationship at least based on the facility procedure volume metric.

Example 35 is a method as in any of Examples 31-34, further comprising calculating a practitioner-facility procedure volume metric indicating a proportion of the practitioner's procedure volume that was provided at the facility over the time period based on the total quantity of the carrier claims billed by the practitioner that indicate the practitioner performed a procedure and a quantity of the carrier claims that identify the practitioner performed a procedure at the facility.

Example 36 is a method as in any of Examples 31-35, further comprising determining whether the practitioner and the facility are in a professional relationship apart from an official ownership or employment relationship at least based on the practitioner-facility procedure volume metric.

Example 37 is a method as in any of Examples 31-36, further comprising: determining whether the practitioner is associated with the facility based on enrollment information in an enrollment database; and determining whether the practitioner is a sole proprietor based on the enrollment information in the enrollment database.

Example 38 is a method as in any of Examples 31-37, wherein determining whether the practitioner is associated with the facility based on the enrollment information comprises determining based on: a unique practitioner ID assigned to the practitioner, wherein the unique practitioner ID is an individual National Provider Identifier (NPI); a unique facility ID assigned to the facility, wherein the unique facility ID is a Centers for Medicare and Medicaid Services Certification Number (CCN); and whether the unique practitioner ID is assigned to the unique facility ID.

Example 39 is a method as in any of Examples 31-38, further comprising: determining whether the practitioner is associated with the facility based on enrollment information in an enrollment database; and determining whether the practitioner and the facility are associated with one another apart from an official ownership or employment relationship based on one or more of: whether the practitioner is associated with the facility in the enrollment database; a facility procedure volume metric indicating a proportion of the facility's procedure volume that was provided by the practitioner over the time period based on the total quantity of the facility claims that indicate a procedure was performed at the facility and a quantity of the facility claims that identify the practitioner performed a procedure at the facility; or a practitioner-facility procedure volume metric indicating a proportion of the practitioner's procedure volume that was provided at the facility over the time period based on the total quantity of the carrier claims billed by the practitioner that indicate the practitioner performed a procedure and a quantity of the carrier claims that identify the practitioner performed a procedure at the facility.

Example 40 is a method as in any of Examples 31-39, further comprising determining whether the enrollment information in the enrollment database is likely stale with respect to real-world relationships between the practitioner and the facility based on one or more of the facility procedure volume metric and the practitioner-facility procedure volume metric.

Example 41 is non-transitory computer readable storage medium storing instructions for execution by one or more processors, wherein the instructions comprise steps for completing any of the methods in Examples 1-40.

Example 42 is one or more processors configurable to execute instructions, wherein the instructions comprise steps for completing any of the methods in Examples 1-40.

Example 43 is means for performing any of the method steps in Examples 1-40.

In the above disclosure, reference has been made to the accompanying drawings, which form a part hereof, and in which is shown by way of illustration specific implementations in which the disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium, which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, televisions, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. The terms "modules" and "components" are used in the names of certain components to reflect their implementation independence in software, hardware, circuitry, sensors, or the like. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein purposes of illustration and are not intended to be limiting. Embodiments of the present disclosure may be implemented in further types of devices, as would be known to persons skilled in the relevant art(s).

At least some embodiments of the disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:
1. A method comprising:
aggregating data from a plurality of different data sources, wherein the aggregated data comprises raw data ingested from an external data source in an encrypted format, and wherein the raw data comprises raw carrier claims data;
translating the raw data by de-encrypting the raw data from the encrypted format to a de-encrypted format;
cleaning the de-encrypted raw data by removing at least a portion of the de-encrypted raw data to generate clean data;
generating a modeled version of the clean data by generating an intermediary file within a database, wherein the modeled version is stored in a single table stored on the database, and wherein the intermediary file comprises information for determining whether a practitioner is associated with a clinic based on carrier claims processed by the practitioner;
querying the database to identify the clinic associated with the practitioner by assessing the carrier claims processed by the practitioner over a time period, wherein the carrier claims are stored in the single table comprising the modeled version of the clean data;
calculating a quantity of the carrier claims that identify the clinic to determine a quantity of clinic claims;
calculating a total quantity of carrier claims processed by the practitioner over the time period; and
determining whether the practitioner is associated with the clinic based on the quantity of clinic claims and the total quantity of carrier claims;
wherein determining whether the practitioner is associated with the clinic reflects real-world associations between the practitioner and the clinic given in real-time based on carrier claims processed by the practitioner.

2. The method of claim 1, further comprising:
identifying a practitioner ID associated with the practitioner;
identifying a clinic ID associated with the clinic; and
reading an enrollment database to determine whether the practitioner ID is assigned to the clinic ID.

3. The method of claim 2, further comprising determining a likelihood the practitioner is a member of the clinic based on:
the quantity of clinic claims;
the total quantity of carrier claims processed by the practitioner over the time period; and
whether the practitioner ID is assigned to the clinic ID within the enrollment database.

4. The method of claim 2, further comprising determining whether enrollment information for the practitioner and/or the clinic within the enrollment database is stale with respect to the real-world associations between the practitioner and the clinic based on:
the quantity of clinic claims;
the total quantity of carrier claims processed by the practitioner; and
whether the practitioner ID is assigned to the clinic ID within the enrollment database.

5. The method of claim 2, wherein:
the practitioner ID is an individual National Provider Identifier (NPI);
the clinic ID is an organization NPI; and
the enrollment database is a database associated with Provider Enrollment, Chain and Ownership System (PECOS).

6. The method of claim 1, wherein identifying the clinic associated with the practitioner comprises querying the database to identify carrier claims processed by the practitioner that identify one or more distinct clinic IDs.

7. The method of claim 1, wherein calculating the quantity of clinic claims comprises reading the carrier claims and counting a quantity of the carrier claims that include a clinic ID associated with the clinic.

8. The method of claim 1, further comprising calculating a clinic proportion by calculating a total number of the carrier claims processed by the practitioner that include a clinic ID associated with the clinic; and
wherein determining whether the practitioner is associated with the clinic comprises determining based on the clinic proportion.

9. The method of claim 8, further comprising:
determining whether the clinic proportion meets a threshold; and
in response to the clinic proportion meeting the threshold, determining that the practitioner is professionally associated with the clinic.

10. The method of claim 9, further comprising:
in response to the clinic proportion meeting the threshold, determining whether the practitioner is assigned to the clinic within an enrollment database; and
determining whether data for the practitioner in the enrollment database is stale with respect to the real-world associations between the practitioner and the clinic based on the carrier claims processed by the practitioner.

11. Non-transitory computer readable storage medium storing instructions for execution by one or more processors, the instructions comprising:
aggregating data from a plurality of different data sources, wherein the aggregated data comprises raw data ingested from an external data source in an encrypted format, and wherein the raw data comprises raw carrier claims data;
translating the raw data by de-encrypting the raw data from the encrypted format to a de-encrypted format;
cleaning the de-encrypted raw data by removing at least a portion of the de-encrypted raw data to generate clean data;
generating a modeled version of the clean data by generating an intermediary file within a database, wherein the modeled version is stored in a single table stored on the database, and wherein the intermediary file comprises information for determining whether a practitioner is associated with a clinic based on carrier claims processed by the practitioner;
querying the database to identify the clinic associated with the practitioner by assessing the carrier claims processed by the practitioner over a time period, wherein the carrier claims are stored in the single table comprising the modeled version of the clean data;
calculating a quantity of the carrier claims that identify the clinic to determine a quantity of clinic claims;
calculating a total quantity of carrier claims processed by the practitioner over the time period; and
determining whether the practitioner is associated with the clinic based on the quantity of clinic claims and the total quantity of carrier claims;
wherein determining whether the practitioner is associated with the clinic reflects real-world associations between the practitioner and the clinic given in real-time based on carrier claims processed by the practitioner.

12. The non-transitory computer readable storage medium of claim 11, wherein the instructions further comprise:
identifying a practitioner ID associated with the practitioner;
identifying a clinic ID associated with the clinic; and
reading an enrollment database to determine whether the practitioner ID is assigned to the clinic ID.

13. The non-transitory computer readable storage medium of claim 12, wherein the instructions further comprise determining a likelihood the practitioner is a member of the clinic based on:
the quantity of clinic claims;
the total quantity of carrier claims processed by the practitioner over the time period; and
whether the practitioner ID is assigned to the clinic ID within the enrollment database.

14. The non-transitory computer readable storage medium of claim 12, wherein the instructions further comprise determining whether enrollment information for the practitioner and/or the clinic within the enrollment database is stale with respect to the real-world associations between the practitioner and the clinic based on:
the quantity of clinic claims;
the total quantity of carrier claims processed by the practitioner; and
whether the practitioner ID is assigned to the clinic ID within the enrollment database.

15. The non-transitory computer readable storage medium of claim 12, wherein:
the practitioner ID is an individual National Provider Identifier (NPI);
the clinic ID is an organization NPI; and
the enrollment database is a database associated with Provider Enrollment, Chain and Ownership System (PECOS).

16. The non-transitory computer readable storage medium of claim 11, wherein the instructions are such that identifying the clinic associated with the practitioner comprises querying the database to identify carrier claims processed by the practitioner that identify one or more distinct clinic IDs.

17. The non-transitory computer readable storage medium of claim 11, wherein the instructions are such that calculating the quantity of clinic claims comprises reading the carrier claims and counting a quantity of the carrier claims that include a clinic ID associated with the clinic.

18. The non-transitory computer readable storage medium of claim 11, wherein the instructions further comprise calculating a clinic proportion by calculating a total number of the carrier claims processed by the practitioner that include a clinic ID associated with the clinic; and
wherein determining whether the practitioner is associated with the clinic comprises determining based on the clinic proportion.

19. The non-transitory computer readable storage medium of claim 18, wherein the instructions further comprise:
determining whether the clinic proportion meets a threshold; and
in response to the clinic proportion meeting the threshold, determining that the practitioner is professionally associated with the clinic.

20. The non-transitory computer readable storage medium of claim 19, wherein the instructions further comprise:
in response to the clinic proportion meeting the threshold, determining whether the practitioner is assigned to the clinic within an enrollment database; and
determining whether data for the practitioner in the enrollment database is stale with respect to the real-world associations between the practitioner and the clinic based on the carrier claims processed by the practitioner.

* * * * *